United States Patent
Hess et al.

(10) Patent No.: US 10,928,478 B2
(45) Date of Patent: Feb. 23, 2021

(54) METHODS FOR MONITORING MOTION USING MULTI-TRANSMIT ELECTRICAL COUPLING IN IMAGING OF THE SUBJECT

(71) Applicant: Oxford University Innovation Limited, Oxford (GB)

(72) Inventors: Aaron Hess, Oxford (GB); Matthew Robson, Oxford (GB); Sven Jaeschke, Oxford (GB)

(73) Assignee: OXFORD UNIVERSITY INNOVATION LIMITED (GB)

(*) Notice: Subject to any disclaimer, the term of this patent is extended or adjusted under 35 U.S.C. 154(b) by 0 days.

(21) Appl. No.: 16/423,320

(22) Filed: May 28, 2019

(65) Prior Publication Data

US 2019/0361082 A1 Nov. 28, 2019

Related U.S. Application Data

(60) Provisional application No. 62/676,651, filed on May 25, 2018.

(51) Int. Cl.
| | |
|---|---|
| *G01V 3/00* | (2006.01) |
| *G01R 33/567* | (2006.01) |
| *G01R 33/56* | (2006.01) |
| *G01R 33/561* | (2006.01) |
| *G06T 11/00* | (2006.01) |
| *A61B 5/055* | (2006.01) |
| *A61B 5/00* | (2006.01) |
| *G01R 33/48* | (2006.01) |

(52) U.S. Cl.
CPC .......... *G01R 33/5673* (2013.01); *A61B 5/055* (2013.01); *A61B 5/721* (2013.01); *G01R 33/4816* (2013.01); *G01R 33/5608* (2013.01); *G01R 33/5615* (2013.01); *G06T 11/005* (2013.01); *G06T 2210/41* (2013.01)

(58) Field of Classification Search
CPC .............. G01R 33/543; G01R 33/5659; G01R 33/3415; G01R 33/36; A61B 5/055
USPC ......................................................... 324/309
See application file for complete search history.

(56) References Cited

U.S. PATENT DOCUMENTS

| | | | | |
|---|---|---|---|---|
| 6,034,990 A * | 3/2000 | Kang | ..................... | H04B 1/408 375/219 |
| 6,411,646 B1 * | 6/2002 | Walley | ..................... | H04B 1/30 375/140 |
| 8,570,507 B1 * | 10/2013 | Cooper | ..................... | G01J 3/44 356/301 |
| 2008/0004518 A1 * | 1/2008 | Stehning | ................ | G01R 33/50 600/410 |
| 2012/0256628 A1 * | 10/2012 | Wong | ................. | G01R 33/4836 324/309 |

(Continued)

FOREIGN PATENT DOCUMENTS

| | | | | |
|---|---|---|---|---|
| JP | 01015034 A | * | 1/1989 | ............. A61B 10/08 |

OTHER PUBLICATIONS

Nagao, Masataka JP-01015034-A Jan. 19, 1989 JP (Year: 1989).*

*Primary Examiner* — Walter L Lindsay, Jr.
(74) *Attorney, Agent, or Firm* — Thomas | Horstemeyer, LLP

(57) ABSTRACT

Described herein are methods for monitoring and/or extracting subject motion from multi-channel electrical coupling in imaging of the subject, in particular in magnetic resonance (MR) imaging of the subject.

20 Claims, 12 Drawing Sheets
(10 of 12 Drawing Sheet(s) Filed in Color)

(56) References Cited

U.S. PATENT DOCUMENTS

| | | | |
|---|---|---|---|
| 2013/0116545 A1* | 5/2013 | Xu | A61B 5/0402 600/413 |
| 2013/0204123 A1* | 8/2013 | Feinberg | A61B 5/055 600/419 |
| 2014/0113577 A1* | 4/2014 | Behrendt | H04B 17/101 455/115.2 |
| 2014/0141784 A1* | 5/2014 | Schmidt | H04W 36/32 455/437 |
| 2014/0218028 A1* | 8/2014 | Snyder | G01R 33/4833 324/309 |
| 2015/0137808 A1* | 5/2015 | Park | G01R 33/5602 324/309 |
| 2016/0161578 A1* | 6/2016 | Weissler | G01R 33/56 324/309 |
| 2016/0307301 A1* | 10/2016 | Zhou | G01R 33/4836 |
| 2016/0378132 A1* | 12/2016 | Daghighian | G06F 13/16 713/503 |

* cited by examiner

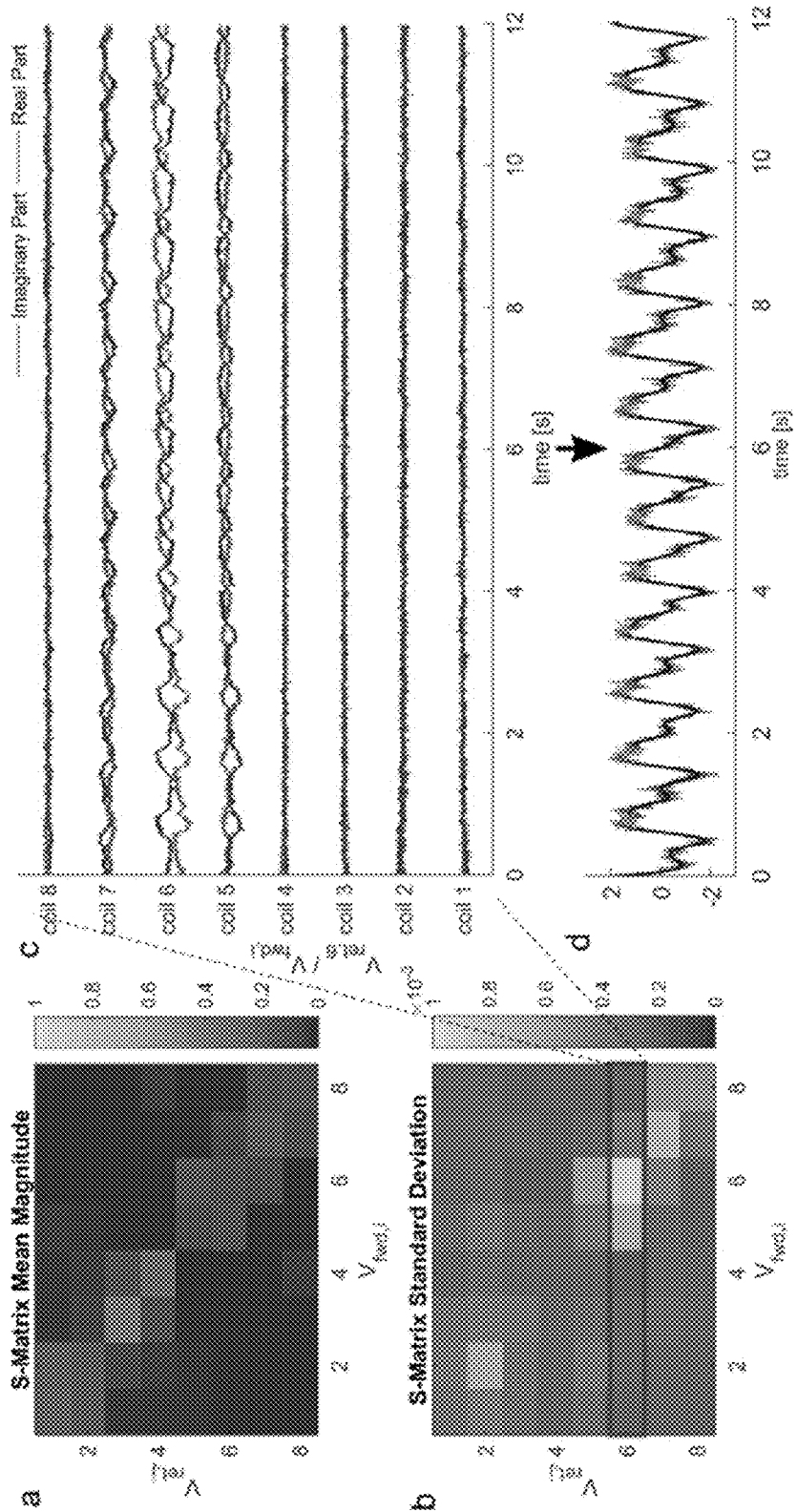

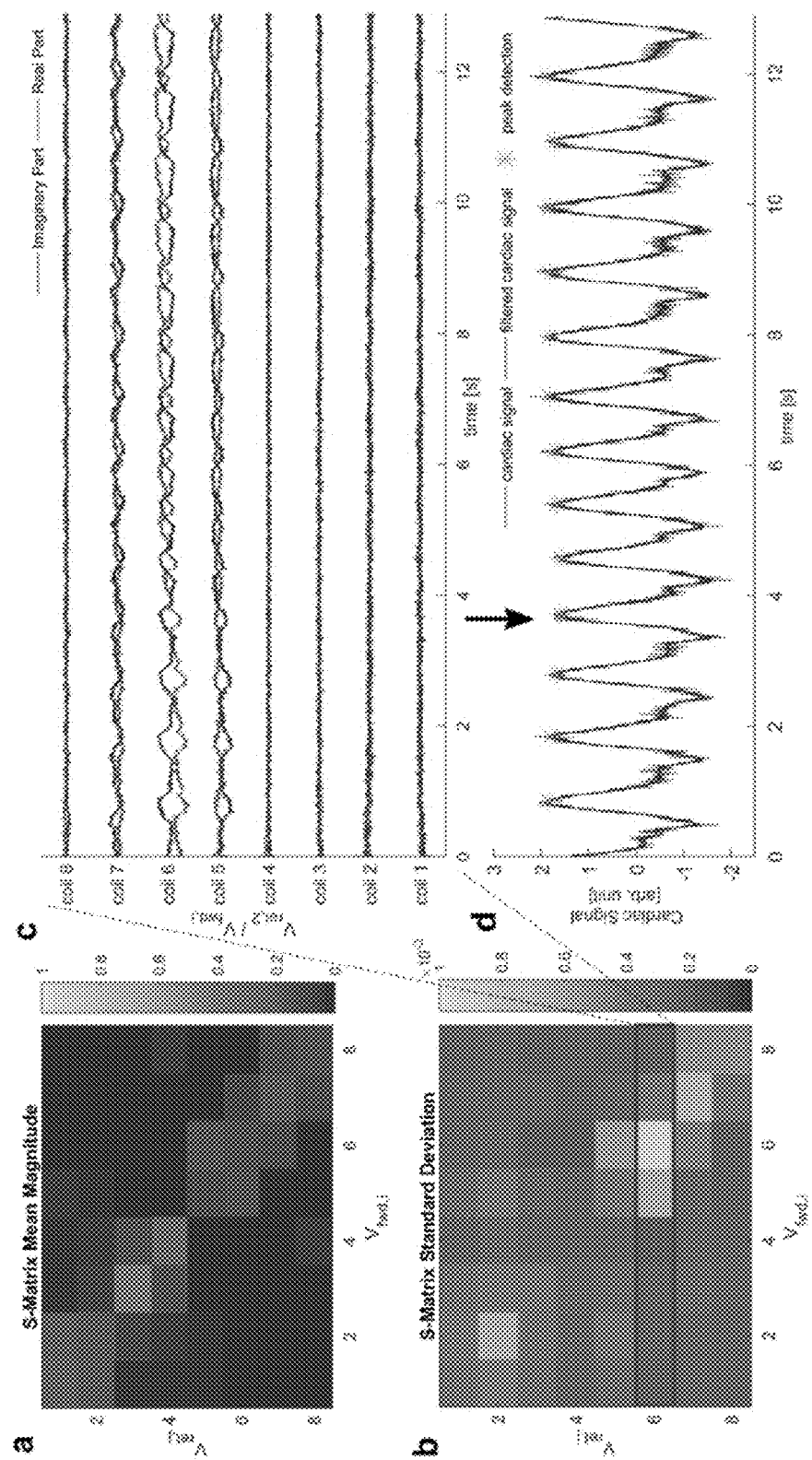

… (1)

METHODS FOR MONITORING MOTION USING MULTI-TRANSMIT ELECTRICAL COUPLING IN IMAGING OF THE SUBJECT

CROSS-REFERENCE TO RELATED APPLICATION

This application claims the benefit of U.S. Provisional Patent Application No. 62/676,651, filed May 25, 2018, which is entirely incorporated herein by reference.

TECHNICAL FIELD

The present disclosure generally relates to methods for extracting or determining patient motion from multi-transmit electrical scattering, in particular in magnetic resonance imaging.

BACKGROUND

Magnetic resonance (MR) imaging (MRI) is a common non-invasive imaging modality useful for structural and functional imaging of living subjects. Subjects to be imaged (or scanned) are placed within or adjacent to a scanner, a magnetic field is applied, and one or more radio frequency (RF) pulses are generated that excite and align proton spins. Following the RF pulse(s), protons relax, generating RF emissions that are detected by receivers in the scanner, and an image is generated.

MRI quality is particularly subject to voluntary and involuntary motion of a subject in a scanner. Subject motion can create artefacts and issues with image reconstruction, and given the cost and length of MR procedures, subject motion is not desirable. While minimizing voluntary motion is relatively straightforward, minimizing involuntary motion is not. Two main sources of involuntary motion in a subject are the movement of the diaphragm during respiration and the movement of the heart during cardiac cycles. Breath holding is the common method used to minimize involuntary motion of a subject during MRI. Breath holding to minimize diaphragm movement, however, limits scan time (at most 15 seconds in most cases). Controlling for cardiac motion during cardiac cycles requires external hardware, which can be complex (requiring additional technicians) and can slip out of place during a scan.

Accordingly, there is a need to address the aforementioned deficiencies and inadequacies. New methods and systems to minimize motion during MR scanning and improve MRI quality are desired.

SUMMARY

The present disclosure is directed to improving imaging quality, in particular imaging quality of a subject. In various aspects, a method is provided to monitor changes in the position of a subject's (for example, a patient's) organs by measuring how external RF coils couple to the subject and to one another during imaging. Changes in position influence this coupling and are reflected in the scattering of the network of coils. By measuring the scattering whilst also collecting images, for example rapid MRI images, mappings can be generated that describe subject motion as a function of the scattering.

In an embodiment, a method for extraction of subject motion from multi-transmit electrical coupling in magnetic resonance (MR) imaging of the subject is provided. The method can comprise: positioning a subject in association with a magnetic resonance scanner, wherein the magnetic resonance scanner has a plurality of transmit coils; starting one or more MR imaging pulse sequences with the scanner, wherein the one or more MR imaging pulse sequences each comprise a plurality of imaging RF pulses; starting one or more monitoring schemes with the scanner, wherein the one or more monitoring schemes comprise a plurality of monitoring RF pulses overlaid on the one or more MR imaging pulse sequences; collecting one or more scattering matrix (S-matrix) measurements over a period of time using the scanner, wherein the one or more S-matrix measurements include measured information from the one or more imaging RF pulses overlaid with the plurality of monitoring RF pulses; extracting one or more subject motion signals from the one or more S-matrix measurements; reconstructing one or more images of a region of interest (ROI) of the subject gated to the one or more subject motion signals; and outputting the reconstructed images.

In any one or more aspects, the overlaid monitoring RF pulses can include a frequency offset in relation to the centering frequency of the MR imaging pulse sequences selected to avoid interference with an imaging slice of the MR imaging pulse sequences to avoid off-resonance excitation in the imaged object (for example, the ROI of the subject), and wherein the monitoring RF pulses include a sufficient frequency spacing to cope with potential sidelobes. The overlaid monitoring RF pulses can include an Orthogonal Frequency Multiplexing (ORM) monitoring scheme using frequency modulation RF-pulses for each transmit channel for each of the transmit coils. The overlaid monitoring RF pulses can include ultra-short RF pulses, alternated in a pseudo-random fashion in the real and imaginary domain to create pseudo-noise in the frequency domain of the monitoring RF pulses. The overlaid monitoring RF pulses can include a random spike pattern (RSP) scheme based on channel-independent noise patterns. The overlaid monitoring RF pulses can include a time-division multiplex (TDM) scheme that allocates different timeslots for each transmit channel for each of the transmit coils and transmits a monitoring pulse at one channel at a time. The plurality of imaging RF pulses can be part of a gradient echo (GRE) sequence, an inversion recovery sequence, or a balanced steady state free precession sequence, individually or in combination. The plurality of imaging RF pulses can be frequency multiplexed pulses, parallel transmit spokes, or parallel transmit spirals, individually or in combination. The each of the plurality of imaging RF pulses can be the same on each individual transmit coil of the plurality of transmit coils of the scanner. An imaging RF pulse on at least one individual transmit coil of the plurality of transmit coils can be different than the pulses on the other transmit coils of the plurality of transmit coils. The plurality of monitoring RF pulses can comprise random and/or pseudo-random spike pattern RF pulses at an offset frequency from the center frequency of one or more MR imaging pulses of about 0.001 hz to about 500 khz. The plurality of monitoring RF pulses can have an ultra-short duration of less than about 10 µs. The sum of the amplitudes of the monitoring RF pulses can be zero, or the induced net magnetization from the monitoring RF pulses can be zero, or both. The one or more monitoring schemes can be configured to avoid inducing interference with the image excitation by the monitoring RF pulses keeping interference, if present, below a noise floor of the image excitation. Each of the plurality of monitoring RF pulses can be different on each individual channel of each transmit coil of the plurality of transmit coils of the scanner and can differ by a channel offset. The channel offset can be a time offset, a frequency offset, or both. The channel offset can be a natural-number multiple of the reciprocal of the monitoring pulse length. The monitoring RF pulse signals on each channel can be configured to not interfere with each other and the sum of dot products of each channel is zero. The one or more subject motion signals can be a cardiac signal, a respiratory signal, or both. One of the one or more subject motion signals can be a cardiac signal identified with an independent component analysis. One of the one or more subject motion signals can be a respiratory signal identified with a principal component analysis.

In an embodiment, a system is provided. The system can extract subject motion from multi-transmit electrical coupling in magnetic resonance imaging of a subject. The system can comprise at least one magnetic resonance scanner, at least one computing device and an application executable in the at least one computing device. The application can comprise logic that can carry out any one or more of the aforementioned features of the method.

In an embodiment, a computer readable medium, in particular a non-transitory computer readable medium, is provided. The medium can employ a program executable in at least one computing device comprising code that can carry out any one or more of the aforementioned features of the system or method, or both.

Other systems, methods, features, and advantages of the present disclosure for extracting or determining subject motion from multi-transmit electrical coupling in imaging of the subject, will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

The patent or application file contains drawings executed in color. Copies of this patent or patent application publication with color drawings will be provided by the Office upon request and payment of the necessary fee.

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1C illustrates a simulated transverse magnetisation (Mxy) using Bloch Simulations that show a broad bandwidth excited in a pseudo-noise way.

FIGS. 2A-2D: FIGS. 2A-2B depict mean magnitude of the scattering matrix (S-matrix) and standard deviation measured using the overlaid spikes (20% amplitude) during an image acquisition. In FIG. 2C one column of the scattering matrix is shown with the scattering on channel 6, originating from all transmit channels. The highest variation can be found between adjoined coils 5-8 which were placed anterior on the chest, close to the heart of the volunteer subject. In FIG. 2D the filtered (black) and raw (blue) cardiac signals, extracted using an independent component analysis, are shown. Green stars indicate the main peaks of the signal which were used for retrospective cardiac gating and image reconstruction.

FIGS. 3B-3E are reconstructed images using spike amplitudes ranging from 5% to 20% of that of the imaging RF pulse.

FIG. 4A is a simulated sensitivity map of a coil placed anterior on the chest, and FIG. 4B is a simulated conductivity distribution in the upper body.

FIG. 8A shows the real component and FIG. 8B the imaginary component.

FIGS. 9A-9D: FIG. 9A shows mean magnitude and FIG. 9B standard deviation of the S-matrix measured using the overlaid spikes (20% amplitude) during image acquisition. In FIG. 9C one column of the scattering matrix is shown with the scattering on channel 6, originating from all transmit channels. The highest variation can be found in adjoined coils 5-8 which were placed anterior on the chest, close to the heart of the volunteer. In FIG. 9D the filtered (black) and raw (blue) cardiac signal, extracted using the S-matrix measurements, are shown. Green stars indicate the main peaks of the signal which were used for retrospective cardiac gating and image reconstruction.

In FIGS. 10B-10E reconstructed images using monitoring amplitudes ranging from 5% to 20% of that of the imaging RF pulse. Diastole images (left) and pseudo M-modes (right) are shown for each acquired dataset.

DETAILED DESCRIPTION

Figure 1A:
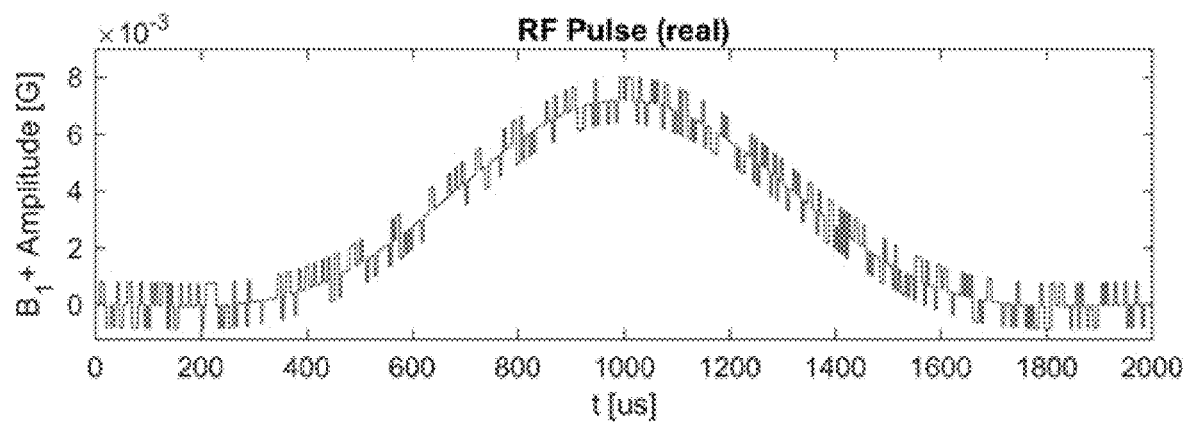
FIGS. 1A-1C show a modified imaging RF-pulse using randomly orientated, ultra-short spikes with an amplitude of 10% of that of the underlying Sinc pulse. The real (FIG. 1A) and imaginary (FIG. 1B) parts of the modified RF-pulse are shown.

Described below are methods for extracting subject motion from multi-channel electrical coupling in imaging of the subject. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It is to be understood that, unless otherwise indicated, the present disclosure is not limited to particular types of methods and systems relating for extracting subject motion in imaging of the subject, and particular software[s] for post-processing and analysis, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a scanner" includes a plurality of scanners. In this specification and in the claims that follow, reference will be made to a number of terms that shall be defined to have the following meanings unless a contrary intention is apparent.

Description

Subject motion during magnetic resonance (MR) imaging scans can create artefacts and issues with image reconstruction. Given the cost and length of MR procedures, subject motion is not desirable. While minimizing voluntary motion is relatively straightforward, minimizing involuntary motion is not. As commented earlier, two main sources of involuntary motion in a subject are the movement of the diaphragm during respiration and the movement of the heart during cardiac cycles. Breath holding is the common method used to minimize involuntary motion of a subject during MRI. Breath holding to minimize diaphragm movement, however, limits scan time (at most 15 seconds in most cases). Controlling for cardiac motion during cardiac cycles requires external hardware, which can be complex (requiring additional technicians) and can slip out of place during a scan.

The current go-to method for cardiac MRI synchronisation is the electrocardiogram (ECG) which is possible at 7T MRI, but lead re-positioning from external (to the imaging scanner) hardware is frequently required (1) and increases subject setup time. Methods and systems herein provide improvements upon existing systems and methods at least by allowing subject monitoring (of the heart and/or diaphragm, for example) without the need for external monitoring hardware which is not part of the imaging scanner. Systems and methods as described herein therefore additionally improve subject scanning by reducing the setup time for subject scans. Monitoring subject motion during scanning can additionally improve the image quality of the scan which is outputted to an external display.

Provided herein are systems and methods to monitor changes in subject motion relating to imaging, for example magnetic resonance (MR) imaging, of a subject. In any one or more aspects, motion can be of a subject or a region of interest of subject (such as an organ or specific tissue). In any one or more aspects, the subject can be a human patient. As described herein, changes in the position of the subject and the subject's organs can be monitored by measuring how external RF coils couple to the subject and one another and change the scattering of one or more RF coils. Changes in position influence this coupling, and the scattering and can be detrimental to the quality of the imaging.

Changes in electrical scattering can be due to movement of the conductive components of the subject's body. For example, as a patient within an MR scanner breathes or the heart beats the conductive elements move around. The RF coils on or adjacent to the surface of the body (that may be already present and used for the imaging) will then couple to each other and the subject in a different way. Existing scanners of various field strengths can contain hardware capable of sensing the forward and reflected power from these coils, and this can be used to dynamically determine the scattering between the RF coils or RF coil network.

By measuring the scattering of the imaging RF pulses overlaid with one or more additional monitoring RF pulses, whilst also collecting images, for example rapid MR images, mappings can be generated that describe subject motion as a function of the scattering. Subsequently the scattering measurements can be used on their own to accurately predict the position of the subject or an ROI of the subject. Effects of drift in the scattering that are not due to subject motion can be monitored and compensated by additional image data, for example additional infrequent MR image data. Knowledge of the subject motion can be used to correct for and obtain better image quality either by using this information to change the acquisition gating (i.e., the timing for pulse initiation and subsequent data acquisition) and/or to change the image reconstruction.

Systems and methods as described herein provide for improvements in existing systems and methods for generating and acquiring MR images. Systems and methods as described herein can be used to improve MR image quality when imaging subjects by controlling and/or compensating for subject motion. Motions that can influence scattering and that can be corrected can include breathing, cardiac, and involuntary motions (i.e. coughing, sneezing, twitching, swallowing, head movements, limb movements, etc.). Scattering measurements that detect these changes can be used on their own to predict subject motion and can provide for better MR images by appropriately gating image acquisition, or they can be used for motion reconstruction to compensate for motion during image reconstruction following acquisition.

Systems and methods as described herein are improvements upon and different from existing systems and methods in several ways. First, in various aspects no additional external hardware connected to the patient is necessarily required, making for faster subject set-up, a safer subject environment (no RF burns from ECG equipment for example), and reduced cost. However, existing hardware has not been utilized to monitor motion in the manner as described below and herein.

Further, systems and methods as described herein monitor more independent characteristics of motion. Existing systems and methods with ECG and respiration monitoring are limited to detecting at most 2 degrees of freedom. In any one or more aspects, the systems and methods as described herein utilize a parallel processing approach with multiple parallel transmitter coils (from 2 to 16 coils or channels, for example) that couple to a subject, providing for more parameters that can be used to provide more detailed measurements than approaches with 2 degrees of freedom. For example, systems and methods as described herein using coil coupling and an 8 channel system can provide for 64 complex valued parameters that can be detected, which provides a more detailed measurement of the subject. Further the present coil coupling approach provides information at a temporal resolution of the RF pulses, which for a rapid SSFP sequence can be around 3 ms temporal resolution.

In any one or more aspects, the systems and methods as described herein improve upon those previously described by at least the use of a multiple channel approach that integrates the information from the multiple channels. As described herein, information from the multiple channels can comprise information from the imaging RF pulses overlaid with one or more monitoring RF pulses. In an aspect 8 channels can be used; however, in other aspects more than 8 channels can be used (for example, up to 16 channels) and fewer than eight channels can be used (for example down to 2 channels). Further, systems and methods as described herein can utilize imaging data to convert the dynamic coupling parameters into useful motion parameters. It is this combined imaging and RF scattering solution and the associated hardware and algorithms which makes this approach so valuable, as it provides a solution that will work in all subjects and so can be readily translated onto clinical scanners (such as MRI scanners) for both image acquisition and image reconstruction.

Systems and methods herein additionally provide improvements upon existing systems and methods by providing high signal-to-noise ratio (SNR), higher than obtained in systems and methods that do not involve the present systems and methods of overlaying imaging RF pulses with one or more monitoring RF pulses. The present systems and methods additionally provide improvements upon existing systems and methods by allowing extraction of and gating to a motion signal such as a cardiac signal and/or a respiratory signal from the subject (relating to cardiac and/or respiratory motion) without the need for an additional motion monitoring sequence (such as a cardiac and/or diaphragm monitoring sequence). The present systems and methods can then be used for retrospective motion gating (for example, retrospective cardiac and/or respiratory gating) to reduce unwanted motion artefacts during image acquisition and improve image quality.

Systems and methods as described herein further improve upon existing systems and methods by providing a monitoring scheme that enables simultaneous measurements of the scattering matrix (S-matrix) of one or more pTx coils of a scanner during image acquisition without prolonging the image sequence and without spin distortion. These monitoring schemes may interfere with the magnetic resonance (MR) sequence but do not interfere or at least provide minimal interference with (below a noise floor of) the image excitation pulse. Systems as described herein also improve the resultant image quality of the scan by minimizing blurring and artefacts in the images that are outputted.

Figure 13:
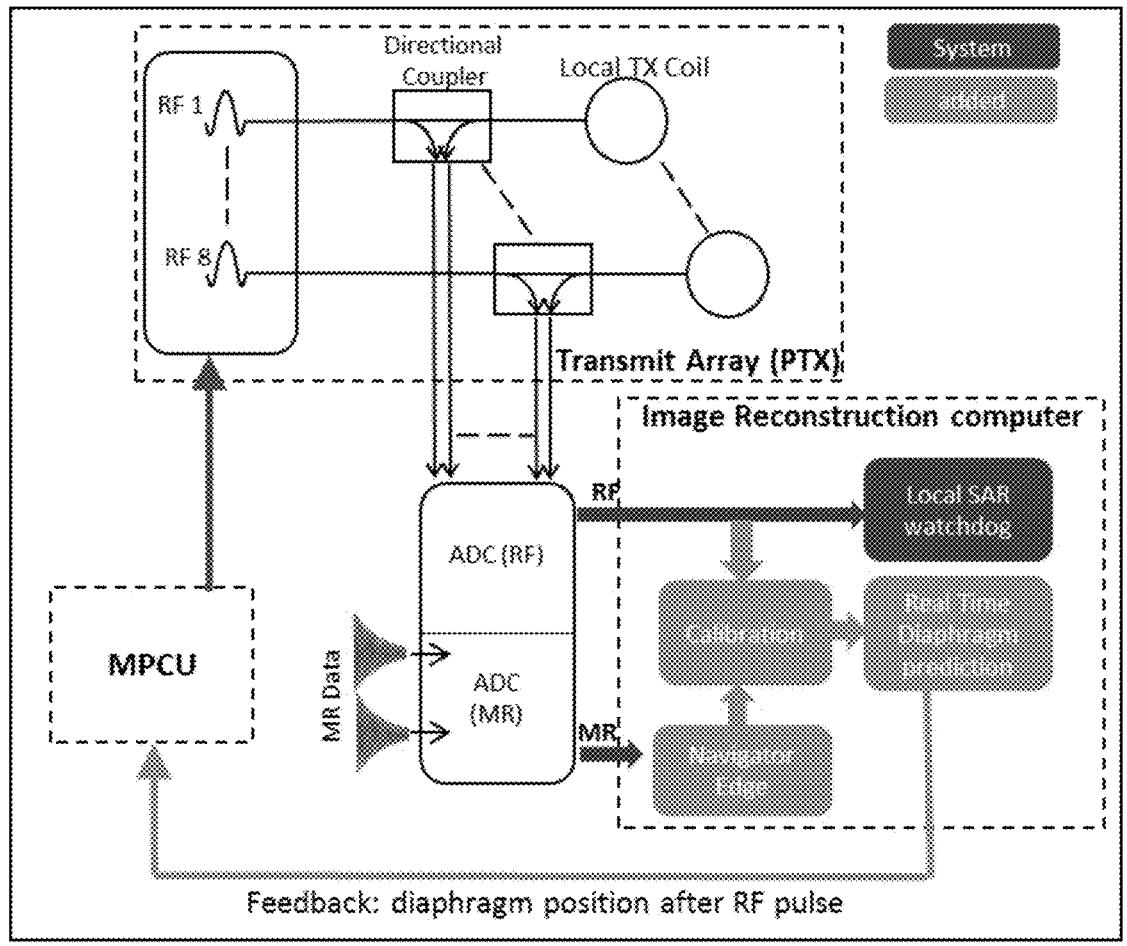
FIG. 13 is a schematic showing an embodiment of a system of the present disclosure. Methods as disclosed herein can be implemented on a system such as this.

Described herein are systems for acquiring and reconstructing MR images that can monitor subject motion. The subject can be, but need not be, a human patient. The subject can also be an animal, plant or inanimate subject. The subject can have a vascular system of interest. In various aspects, the methods and systems herein can comprise an MR scanner with a plurality of transmit channels and an image reconstruction computer (computers and processors described more in depth later in the discussion). They can also comprise a measurement and physiological control unit (MPCU), analog-to-digital converters (ADCs), a specific absorption rate (SAR) monitoring system, and a plurality of RF transmit, receive, or transmit/receive coils that can be positioned near or around a region of interest (ROI) of a subject. In an aspect, there are at least two such RF coils. The components can be configured to send/receive data and/or electromagnetic signals (radio frequency pulses, for example) between each other. FIG. 13 shows a diagram of an embodiment of a system according to the present disclosure that can include such components. While the system of FIG. 13 depicts an embodiment directed to respiratory motion (diaphragm position), one skilled in the art can understand how the system of FIG. 13 can be adapted to monitoring other subject motion, in particular cardiac motion.

The SAR monitoring system is a safeguard of MR scanners to measure the effects of transmitted RF voltages on a subject. As described herein, and as illustrated in FIG. 13, this system can be utilized to monitor subject motion using existing or custom hardware based on reflected power measurements. An SAR system can comprise directional couplers ("dicos", one for each transmit channel) that monitor the forward and returned RF voltage on each transmit channel. Signals in and out of the dicos can be demodulated and digitized by an ADC of the system and delivered in real time to a local SAR monitor (which can comprise software implemented on a computer, such as the image reconstruction computer).

The SAR monitoring system can also comprise a plurality of transmit/receive RF coils in parallel. These coils can capture measurements of the discos before they enter the SAR monitoring system. There can be one transmit/receive coil per transmit channel of the system. In various embodiments, a plurality of parallel transmit/receive RF coils can be from 2 to 16 coils and any member in between. The exact positioning and configuration of the parallel transmit/receive RF coils can be determined by an end user depending on field strength of the MR scanner and subject anatomy (i.e., ROI of the subject). The plurality of parallel transmit/receive coils can electrically couple to a subject during a scan, and the coils can also couple to each other during a scan.

Described herein are methods for monitoring subject motion, for example diaphragm or cardiac motion, during an MR scan. The methods can use a scattering matrix (S-matrix) measured during an RF pulse with a plurality of parallel transmit coils, wherein the S-matrix measurements comprise measured information from one or more imaging RF pulses overlaid with one or more monitoring RF pulses. A method for determining subject motion can use changes in scattering or in the scattering coefficients of scattering matrices of measured returned voltages from RF pulses to track subject motion.

In any one or more aspects, the one or more imaging RF pulse sequences can each comprise a plurality of imaging RF pulses. The imaging RF pulses as described herein can be part of a gradient echo (GRE), inversion recovery, balanced steady state free precession (SSFP), or one or more other pulse sequences, or specifically applied for the purpose of motion measurement, individually or in combination. In embodiments, pulses as described herein can have a shapes characteristic of a sinc, Guass, rectangular, fermi, hyperbolic secant. Pulses as described herein can be the same on each transmit coil or they can be different on each transmit coil, such as frequency multiplexed, parallel transmit spokes, or parallel transmit spirals, individually or in combination.

The plurality of imaging RF pulses can be the same on each individual transmit coil of the plurality of transmit coils of the scanner. An imaging RF pulse on at least one individual transmit coil of the plurality of transmit coils can be different than the pulses on the other transmit coils of the plurality of transmit coils.

In any one or more aspects, monitoring RF pulses as described herein can interfere with the MR sequence itself without interfering with the MR image excitation, or at least keeping below a noise floor of the MR image excitation. Monitoring RF pulses as described herein can be overlaid with the one or more imaging RF pulses sequences. The overlaid monitoring RF pulses can be configured to include a frequency offset in relation to the centering frequency of the MR imaging pulse sequences selected to avoid or at least reduce or minimize interference with an imaging slice of the MR imaging pulse sequences to avoid off-resonance excitation in the imaged object. The monitoring RF pulses can be configured to include a sufficient frequency spacing to cope with potential side-lobes.

The offset frequency for the frequency multiplexing can depend on the imaging pulse bandwidth and the slice select gradient of the MR system. The offset frequency can be set to avoid interference with the imaged object and off-resonance excitation can be outside the field of view of the coil. The upper frequency offset can be limited by the total bandwidth of the system which can be in an embodiment 1 Mhz. (max. 500 kHz). The lower frequency limit can be about 0.001 Hz or more, 0.001 kHz or more. Thus, in various aspects, the offset frequency of the monitoring RF pulses from the center frequency of the one or more MR imaging pulses can be from about 0.001 kHz to about 500 kHz and at any frequency or range of frequencies therebetween. In an embodiment, the frequency offset can be set at 54 kHz.

The overlaid monitoring RF pulses can include an Orthogonal Frequency Multiplexing (OFM) monitoring scheme using frequency modulation RF-pulses for each transmit channel for each of the transmit coils. The monitoring scheme can include a Random Spike Pattern (RSP) scheme or a code division multiplexing scheme. The monitoring scheme can include a time-division multiplex (TDM) scheme. The OFM, RSP, and TDM monitoring scheme may be used individually or in combination.

According the present disclosure, in any one or more aspects, orthogonality can mean that the signals (or the monitoring RF signals on each channel and to the imaging RF-pulse) do not interfere with each other and that their dot products (sum of the products of each element) is zero or near zero. The orthogonality proofs that the RF-waveforms on the channels can be independent of each other. This can be desired for the monitoring RF schemes described herein where it is desired that the created noise patterns are independent for each channel as each monitoring signal can use the same frequency bandwidth. When the created noise patterns are truly orthogonal, the sum of the channels can be zero (or close to zero in an imperfect system/noise pattern) in the frequency domain too.

The frequency multiplexing can also achieve non-interfering pulses when using a relatively large frequency spacing between the different channels.

The overlaid monitoring RF pulses can include ultra-short RF pulses. An example, ultra short pulses can be pulses of less than 2 µs. They can include a pseudo-random pattern on each channel. They can be alternated in a pseudo-random fashion in the real and imaginary domains to create pseudo-noise in the frequency domain of the monitoring RF pulses. The ultra-short RF pulses (with a pseudo-random pattern on each channel) can create a noise-like frequency spectrum. The noise-like frequency spectrum can be white-noise like and therefore can cover the entire bandwidth of the system (in the present case case: 0-500 kHz) with the same magnitude. Longer RF pulses of 2 µs to 10 µs can also be used. For these longer RF pulses the noise spectrum can become less equally distributed but still can have noise-like properties. The induced net magnetization from these patterns can be zero or near zero (sum of the monitoring RF amplitude) and therefore not affect the image (or only have minimum effect on image quality).

In various aspects the monitoring RF pulses can be about 0.1 to about 100 µs and any number or range there between. For example, the RF pulses can be about 1 µs to about 9 µs; the RF pulses can be about 2 µs to about 8 µs; the RF pulses can be about 3 µs to about 7 µs; the RF pulses can be about 4 µs to about 6 µs; the RF pulses can be about 2 µs to about 5 µs. For example, the RF pulses can be about 10 µs to about 90 µs; the RF pulses can be about 20 µs to about 80 µs; the RF pulses can be about 30 µs to about 70 µs; the RF pulses can be about 40 µs to about 60 µs; the RF pulses can be about 20 µs to about 50 µs.

The overlaid monitoring RF pulses can include a random spike pattern (RSP) scheme based on channel-independent noise patterns. In one or more aspects, the plurality of monitoring RF pulses can comprise random spike pattern RF pulses at an offset frequency from the center frequency of one or more MR imaging pulses, for example of about 0.001 Hz to about 500 kHz and any number or range in between. In an embodiment, the offset frequency can be about 27 kHz.

The plurality of monitoring RF pulses can be different on each individual channel of each transmit coil of the plurality of transmit coils of the scanner and differ by a channel offset. The channel offset can be a time offset, a frequency offset, or both.

In various aspects, the channel offset can be a multiple (natural number multiple) of the reciprocal of the monitoring pulse length (time). In this way, the orthogonality criterion and channel independence can be maximised. For example, if a rectangular monitoring pulse with the length of T=1.6 ms is used, the frequency channel spacing can be set as a multiple of f=625 Hz. (which is also the zero-crossing of the side-lobes in the frequency domain). By shifting the channel offset frequencies along the zero-crossing, the interferences can be minimised. As an example channel offset can be a frequency offset of about 5 kHz.

The one or more subject motion signals can be a cardiac signal, a respiratory signal, or both. The one or more subject motion signals can be extracted from the measured S-matrix measurements using a principal component analysis or an independent component analysis. The one or more subject motion signals can also be other body movement that is unwanted during the scan, such as head motion or the subject not lying still, and the like.

Figure 12:
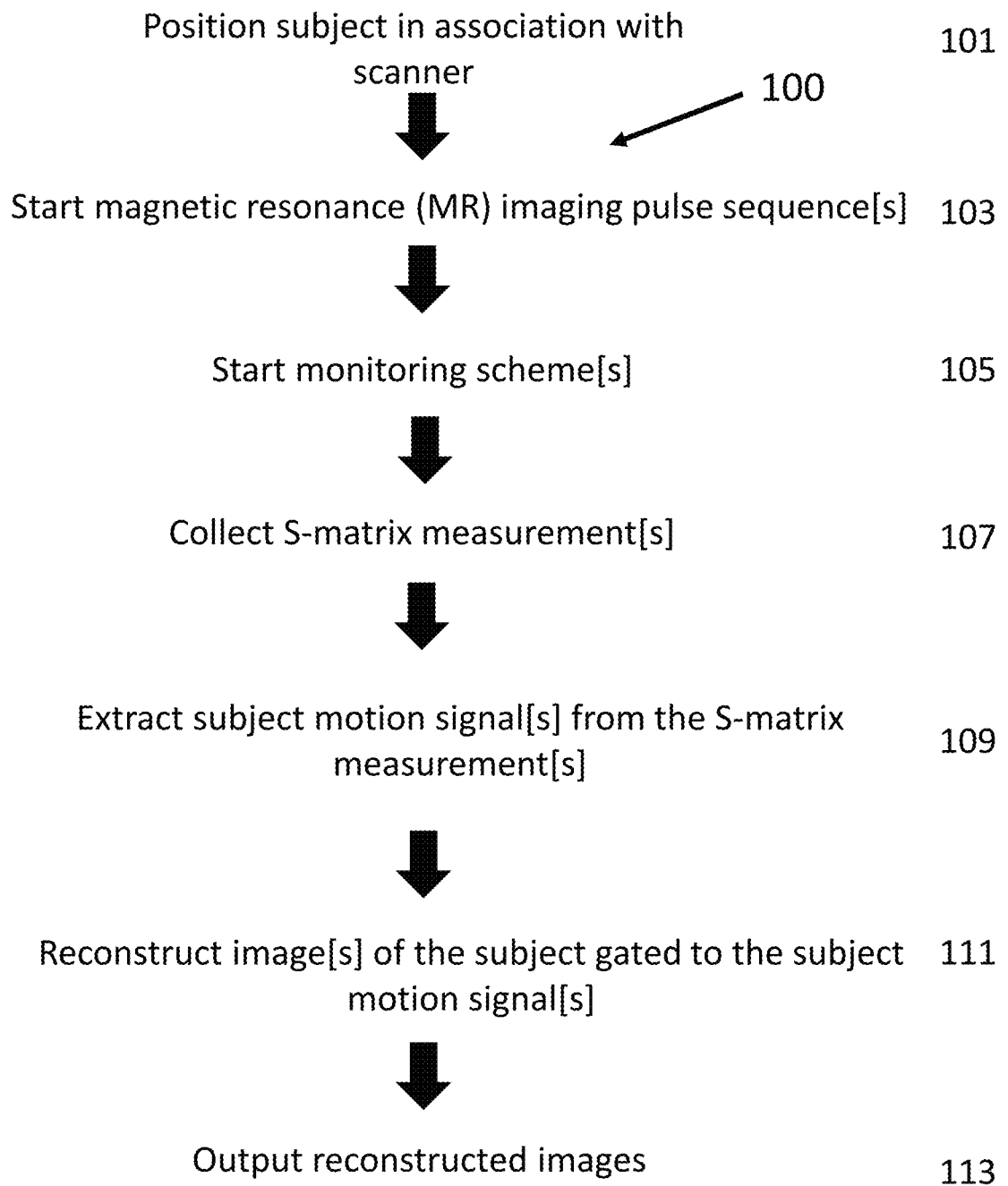
FIG. 12 is a flow chart showing an embodiment of the methods as described herein.

An embodiment of a method 100 to determine or extract a subject position, such as a diaphragm position, is shown in FIG. 12. A subject can be positioned 101 in association with a scanner, for example an MR scanner with a field strength which contains an SAR monitoring system with a commercial parallel transmit (pTX) system containing a plurality of parallel transmit coils. One or more imaging pulse sequences can be initiated 103 with the scanner for performing imaging on an anatomical region of interest of the subject, such as a diaphragm or the heart. The anatomical region of interest can be undergoing motion, for example it can be undergoing motion according to a cycle such as a relax-contract cycle. The motion can be cardiac or respiratory motion. After imaging pulse sequence initiation 103, one or more monitoring schemes 105 can be started prior to acquisition. The one or more monitoring schemes can comprise overlaying a plurality of RF monitoring pulses on the one or more imaging pulse sequences. One or more S-matrix measurements 107 can be collected related to the one or more imaging pulse sequences overlaid with the one or more monitoring schemes 105. The one or more S-matrix measurements can include measured information from the one or more imaging pulse sequences overlaid with the one or more monitoring schemes. One or more subject motion signals 109 can be extracted from the one or more S-matrix measurements 107. The one or more motion signals can be representative of diaphragm motion, heart motion, or both, for example. One or more images of the anatomical region of interest of the subject can be reconstructed 111 that are gated to the one or more subject motion signals 109. The one or more reconstructed images 111 can then be outputted 113, for example to a display of or in communication with the scanner.

Thus, described herein are methods for monitoring subject motion during an MR scan. The methods can use the scattering from an imaging RF pulse with a plurality of parallel transmit coils overlaid with one or more monitoring RF pulses. In one or more aspects, pulses as described herein can be or required to be executed with sufficient transmit amplitude that they can be measured by the directional couplers. They can be repeated as often as required, either as part of the designated pulse sequence (GRE is used in methods shown here) or repeated as and when motion is to be measured. The motion can be cardiac motion and/or respiratory (diaphragm) motion.

Figure 11:
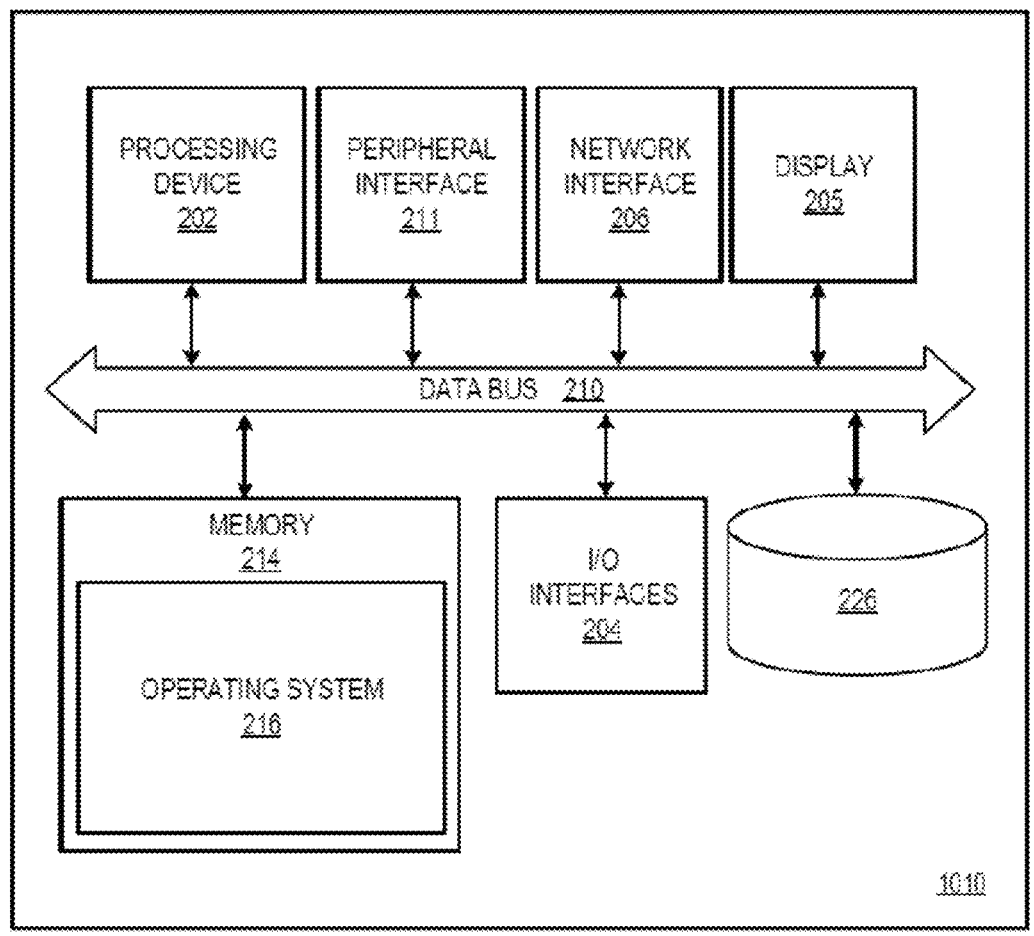
FIG. 11 shows an embodiment of a computing device or apparatus 1010 that can be implemented in the systems as described herein and which can implement methods as described herein.

FIG. 11 depicts an apparatus 1010 in which the systems, analysis systems, breadboard analysis systems, or other systems described herein may be coupled to in order to assist in automation of the system and carrying out the methods described herein. The apparatus 1010 can be embodied in any one of a wide variety of wired and/or wireless computing devices, multiprocessor computing device, and so forth. As shown in FIG. 11, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 can be coupled to one or more peripheral measurement devices (not shown) connected to the apparatus 1010 via the peripheral interface 211.

The processing device 202 can include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications can include application specific software which may be configured to perform some or all of the methods described herein (Labview, for example). In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 can comprise a computer monitor, a plasma screen for a PC, a liquid crystal display (LCD) on a hand held device, or other display device.

In the context of this disclosure, a computer-readable medium (such as a non-transitory computer readable medium) stores programs for use by or in connection with an instruction execution system, apparatus, or device. More specific examples of a computer-readable medium can include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 11, network interface device 206 comprises various components used to transmit and/or receive data over a network environment. For example, the network interface 206 can include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 can communicate with one or more computing devices via the network interface 206 over a network. The apparatus 1010 may further comprise mass storage 226. The peripheral 211 interface supports various interfaces including, but not limited to IEEE-1394 High Performance Serial Bus (Firewire), USB, thunderbolt, a serial connection, and a parallel connection.

The apparatus 1010 shown in FIG. 11 can be embodied, for example, as a magnetic resonance (MR) apparatus, which includes a processing module or logic for performing conditional data processing, and may be implemented either off-line or directly in a magnetic resonance apparatus. For such embodiments, the apparatus 1010 can be implemented as a multi-channel, multi-coil system with advanced parallel image processing capabilities, and direct implementation makes it possible to generate images, for example, immediate T1 maps, available for viewing immediately after image acquisition, thereby allowing re-acquisition on-the-spot if necessary. Examples of apparatus in which the present systems and methods may be implemented are described in U.S. Pat. Nos. 5,993,398 and 6,245,027 and U.S. Publication No. 2011/0181285, which are incorporated by reference as if fully set forth herein.

The flow chart of FIG. 12 shows an example of functionality that can be implemented in the apparatus 1010 of FIG. 11. If embodied in software, each block shown in FIG. 12 can represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 11) in a computer system or other system. The machine code can be converted from the source code, etc. If embodied in hardware, each block may represent a circuit or a number of interconnected circuits to implement the specified logical function(s).

Although the flowchart of FIG. 12 shows a specific order of execution, it is understood that the order of execution may differ from that which is depicted. For example, the order of execution of two or more blocks may be scrambled relative to the order shown. Also, two or more blocks shown in succession in FIG. 12 can be executed concurrently or with partial concurrence. Further, in some embodiments, one or more of the blocks shown in FIG. 12 can be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

FIG. 13 shows an embodiment of scanners (also referred to as scanner systems) according to systems and methods as described herein and that can be incorporated into the systems described herein and used for carrying out the methods described herein. Scanners as described herein can further comprise a display to which images can be outputted for display by a user.

In certain embodiments, methods as described herein can be implemented on the scanner's image reconstruction system. This can consist of an image reconstruction and edge detection for the navigator images, a functional unit to perform the calibration and the online calculation of the diaphragm position from scattering that is transmitted back to the MPCUs of the PTx. These components are shown as "added" in FIG. 13. The image reconstruction system can further comprise a display upon which reconstructed images are outputted to.

In certain embodiments, systems and methods as described herein can comprise a Magnetom 7T (Siemens, Erlangen Germany) equipped with an 8 channel PTx and local SAR monitor (VB17 step 2.3). The local SAR monitor can comprise eight directional couplers, one for each transmit channel that monitor the forward and returned RF voltage on each transmit channel. They can be demodulated by the carrier frequency and connected to the MR receivers' analogue to digital converter that digitizes them at 1 MHz during all RF transmissions. The digitized voltages can be delivered in real time to the local SAR monitor, this is summarised in an embodiment in FIG. 13.

FIG. 13 is a schematic showing components of a local SAR monitor and added software components. In an embodiment, systems as described herein can further comprise a local transmit receive RF coil was built using the transmission line or TEM method, comprising 4 elements positioned posteriorly and 4 anteriorly, each element 15 cm long and separated by 50 mm centre to centre and positioned for maximum coverage of the heart.

EXAMPLES

Now having described various embodiments of the disclosure, in general, the examples below describe some additional embodiments. While embodiments of the present disclosure are described in connection with the examples and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Introduction

The current go-to method for cardiac MRI synchronization is the ECG. While ECG gating is possible at 7T MRI, lead re-positioning is frequently required (1) and increases subject setup time. Missed or false trigger results can increase scan time or degrade image quality.

Recently, it has been shown that the scattering of an eight channel pTx coil can be used for cardiac signal estimation (2) using a dedicated monitoring sequence or the reflection of the imaging RF-pulse which is dependent on B1+ shim (3). In this example herein, a monitoring scheme is provided that incorporates the measurement of the scattering matrix (S-matrix) of a pTx coil into normal image acquisition by overlaying the imaging RF-pulse with small, ultra-short and randomly orientated spikes. It is shown that this new monitoring scheme can lead to high SNR in the cardiac signal and can be used for retrospective cardiac gating for imaging of a subject.

Methods

Measurements were made on a 7T MRI Scanner (VB17, Step 2.3, Siemens 7.0 T Magnetom, Erlangen, Germany) with an 8 channel, dipole cardiac transmit/receive array with four elements placed anterior and four elements placed posterior (ref). Directional couplers (DICOs) are built into each of the RF-transmission lines, as part of the pTx safety system to monitor SAR, to measure the forwarded and reflected RF waveforms.

The relationship between all channels of the coils can be seen as an N-port electrical network which is electrically loaded by the human body. If the imaging object and its complex permittivity distribution change within the field of view of each coil element due to motion, the electrical loading and impedance match change correspondingly (4). The scattering matrix $S_{n,n}$ defines the fractional, returned voltage $V_{i,j,ret}$ on each channel i which originates from the forward voltage ($V_{j,fwd}$) on channel j and thus can be used to monitor those changes induced by motion:

$$V_{i,j,ret} = S_{i,j} V_{j,fwd} \quad [1]$$

Scattering Matrix Measurements S During Image Acquisition

Figure 1B:
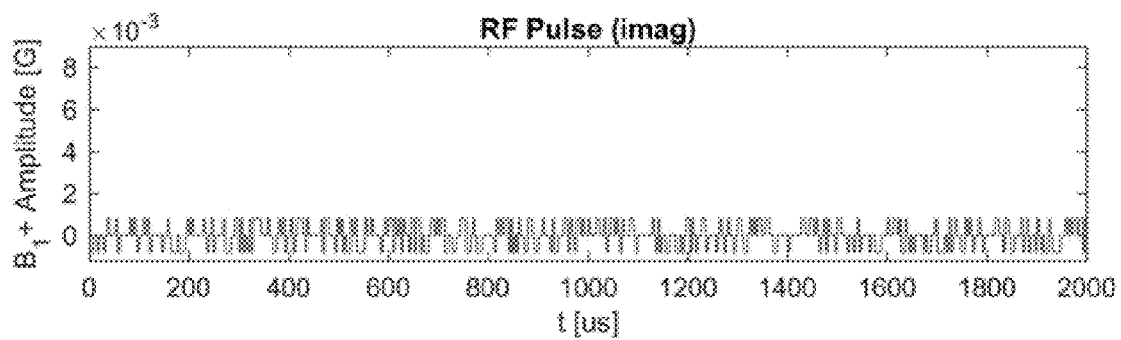
Figure 1C:
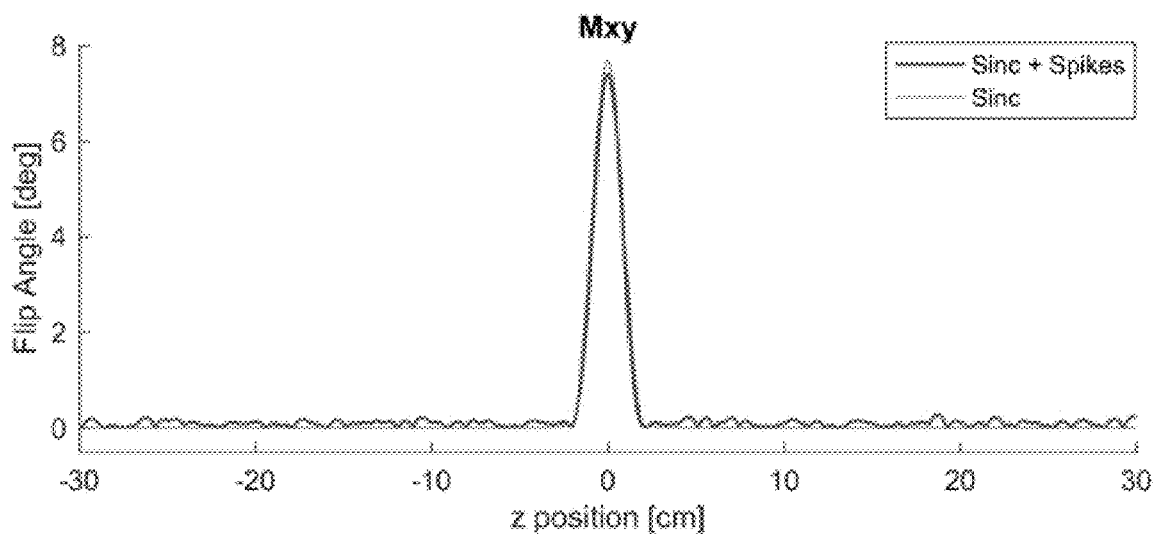
Figure 3A:
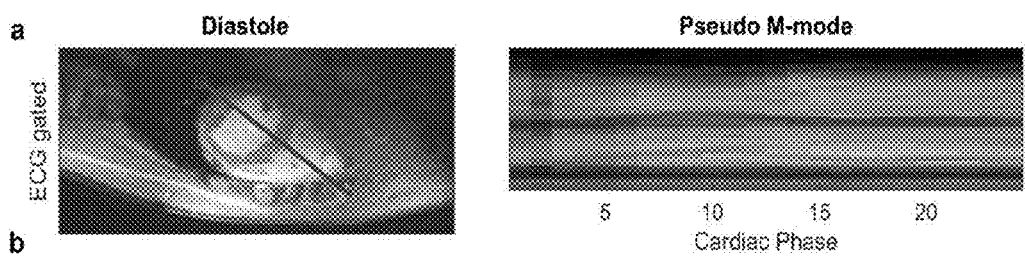
FIGS. 3A-3E depict diastole images and pseudo M-modes. Images were reconstructed using an ECG (FIG. 3A) and the cardiac signal extracted from the scattering matrix.
Figure 3B:
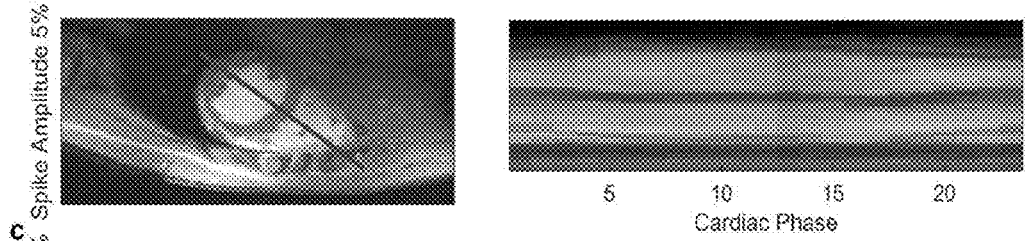
Figure 3C:
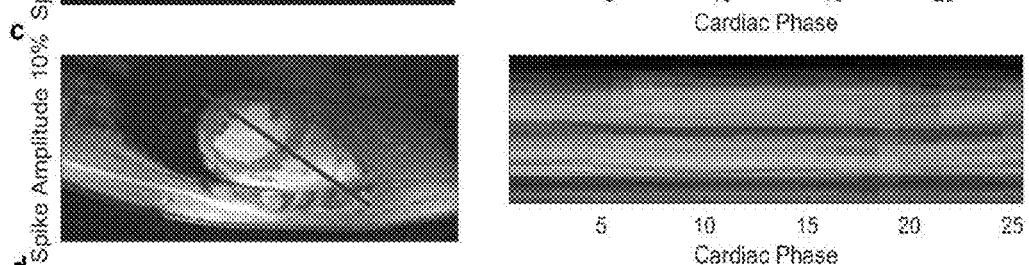
Figure 3D:
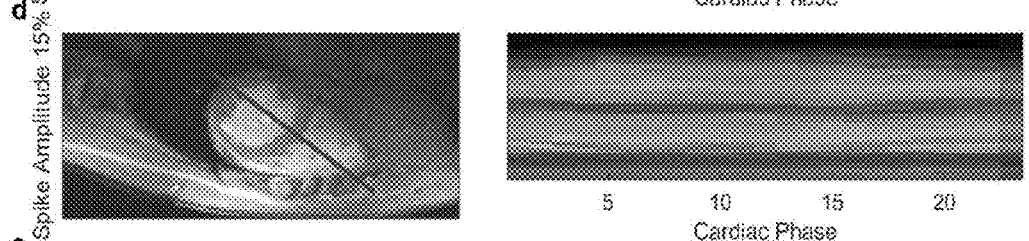
Figure 3E:
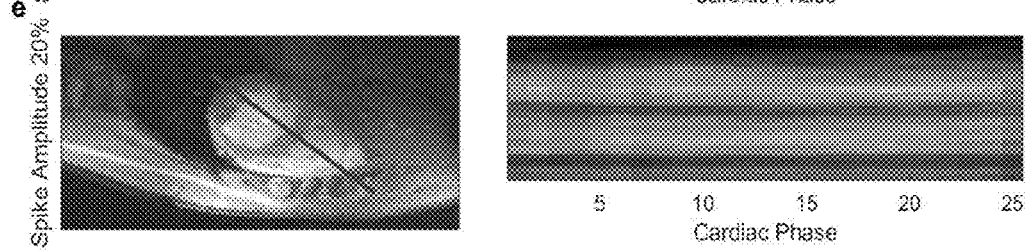

To assess the cardiac signal, a scattering matrix (S-matrix) was measured with ultra-short RF-spikes (td=3 us, amplitude=5-20% of that of the imaging pulse) which were overlaid on the standard imaging RF-pulse to excite a broad bandwidth in the frequency domain, utilizing pseudo-noise. These pulses were alternated in a random fashion, for each channel independently, on the real and imaginary part of the imaging pulse so that the net magnetization remained close to zero. Bloch simulations were carried out to test the expected magnetization effect of the modified pulses (compare FIGS. 1A-1C).

The modified pulses and their distinguishable pattern for each forwarded channel $V_{j,fwd}$, enabled an identification of each $V_{i,j,ret}$ and were used to solve the linear equation system as in Eq. 1 with MATLAB to calculate the S-Matrix for each imaging RF-pulse.

Data Pre-Processing and Cardiac Signal Peak Detection

The S-matrix measurements S(t) were temporally detrended and separated into real and imaginary components. The cardiac signal was extracted using an independent component analysis on the bandpass filtered data and identified by using a power-welch spectrum density estimation with the highest power in the corresponding cardiac frequency band (f=0.6-2.4 Hz). A discrete wavelet transform (symlets, n=5) was used to establish peak detection on the cardiac signal and to identify cardiac trigger events (compare FIGS. 2A-2D) (more details in ref. (2)).

Retrospective Cine

Imaging was performed using a retrospectively gated 2D GRE cine sequence (GRAPPA factor=2; 35 reference lines; TR=34 ms, flipangle=8°) where the RF-pulses were modified, as described above, to enable simultaneous S-matrix measurements. The main peaks of the extracted cardiac signal were utilized for cardiac gating and the k-space data was binned accordingly. The PULSAR MATLAB toolbox V1.1 (5) was used for image reconstruction.

Results

The scattering matrix (S-matrix) was estimated successfully during image acquisition using all modified RF-pulses with different amplitudes. The extracted cardiac signal had a signal-to-noise ratio of 2.6 to 8.3 for a spike amplitude ranging from 5% to 20% respectively. FIGS. 2A-2D show the measured S-matrix and the extracted cardiac signal, obtained using a modified RF-imaging pulse with a spike amplitude of 20%.

All images were successfully reconstructed with minimal artefacts or blurring using the main peak detection on the estimated cardiac signal (compare FIGS. 3A-3E).

Bloch simulations of the modified RF pulses show minimal off-resonance effects on the transverse magnetization (compare FIGS. 2A-2D). For a targeted flip angle of 8 degrees, the noise amplitude ranges between 0.6% and 2.7% and the added energy per pulse ranges from 0.5% to 14% for an overlaid spike amplitude of 5% to 20%, respectively.

Discussion

Simultaneous measurement of the S-matrix of a pTx coil during imaging is possible and the extracted cardiac signal can be estimated for a range of different monitoring amplitudes. The SNR of the extracted cardiac signal may be dependent on the magnitude of the monitoring amplitudes. Although the monitoring scheme added to SAR and noise, the added SAR is minimal, and noise is mainly apparent in off-frequencies (compare FIGS. 1A-1C).

Retrospectively, cardiac gated 2D-CINE images show the suitability of this monitoring scheme at 7T using a range of monitoring amplitudes which all lead to successful image reconstruction with minimal artefacts or blurring.

Conclusion

Small, random, ultra-short RF spikes can be used to monitor the scattering matrix of a pTx coil at 7T MRI and to estimate cardiac motion during normal image acquisition. The incorporation of the scattering matrix enables retrospective cardiac gating of image acquisition without prolonging the sequence and with only minimal effects on SAR and image quality.

REFERENCES—EXAMPLE 1

1. Suttie J J, Delabarre L, Pitcher A, et al. 7 Tesla (T) human cardiovascular magnetic resonance imaging using FLASH and SSFP to assess cardiac function: Validation against 1.5T and 3T. NMR Biomed. 2012; 25:27-34. doi: 10.1002/nbm.1708.

2. Jaeschke S H F, Hess A T, Robson M D. Contact-free Cardiac Motion Estimation using the Scatter of a Parallel Transmit Coil at 7T MRI. In: Proc. Intl. Soc. Mag. Reson. Med. Honolulu; 2017. p. 3262.

3. Jaeschke S H F, Robson M D, Hess A T. Evaluating the Influence of B1-Shimming on Contact-free Cardiac Gating using Scatter of a Parallel Transmit Coil at 7T MRI. In: Proc. Intl. Soc. Mag. Reson. Med. 25; 2017. p. 1131.

4. Buikman D, Helzel T, Roeschmann P. The rf coil as a sensitive motion detector for magnetic resonance imaging. Magn. Reson. Imaging 1988; 6:281-289. doi: 10.1016/0730-725X(88)90403-1.

5. Ji JIMX, Son JBUM, Rane S D. PULSAR: A MATLAB Toolbox for Parallel Magnetic Resonance Imaging Using Array Coils and Multiple Channel Receivers. 1:24-36. doi: 10.1002/cmr.b.

Example 2

Abstract

Provided herein is a new monitoring scheme that enables simultaneous measurements of the scattering matrix of a pTx coil during image acquisition without prolonging the image sequence and without spin distortion. It is shown herein that the use of these monitoring schemes enable motion detection, i.e. of heart motion, which can be used for retrospective gating of imaging of a subject. Preliminary results in 7T MRI are shown with successfully, retrospectively cardiac-gated 2D-CINE images using the present method.

Introduction

Motion Detection

The current go-to method for cardiac MRI synchronization is the ECG which is possible at 7T MRI, but lead re-positioning is frequently required (1) and increases subject setup time. Recently, it has been shown that the scattering of an eight channel pTx coil can be used for cardiac signal estimation and cardiac gating of image acquisition, using a dedicated monitoring sequence (2) or the scattering coefficients of the imaging RF-pulse (3), which is dependent on B1+ shim (4). In this example, provided herein are monitoring schemes that enable the measurement of the scattering matrix (S-matrix) of a pTx coil during normal image acquisition. Applied to cardiac motion estimation, it leads to a high SNR of the extracted cardiac signal without the need for additional monitoring pulses (as in reference (2)).

Theory

The basis of these techniques presented in this example, were outlined in more detail in references (3,5). In brief, the S-matrix describes an N-port electrical network of the pTx coil, loaded by the human body, and defines the fractional, returned voltage $V_{i,j,ret}$ on each channel i which originates from the forward voltage ($V_{j,fwd}$) on channel j:

$$V_{i,j,ret} = S_{i,j} V_{j,fwd} \quad [1]$$

Figure 4A:
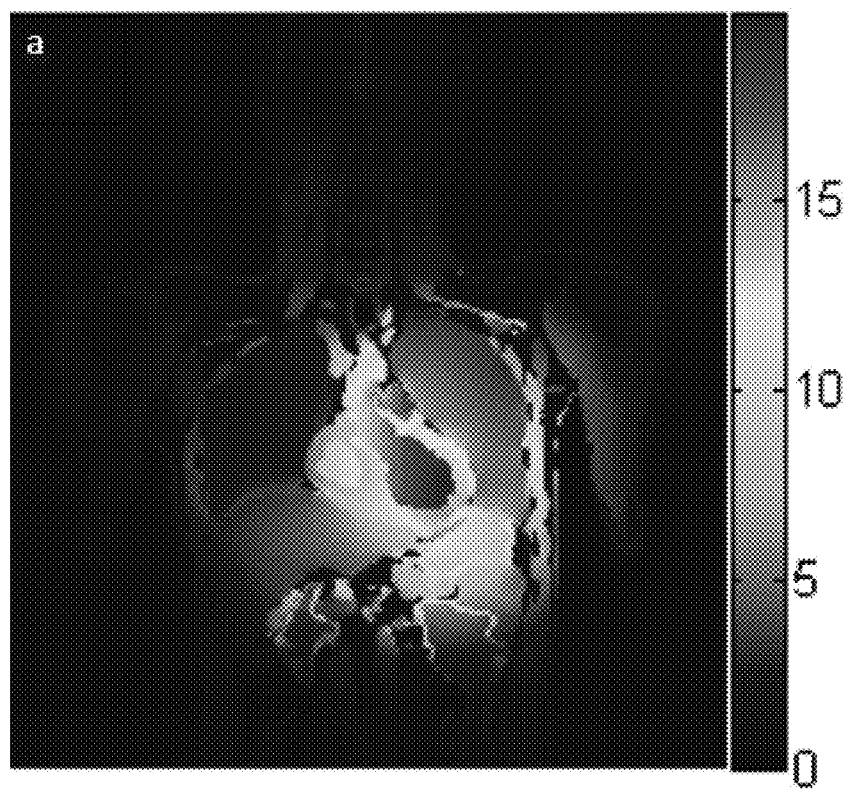
FIGS. 4A-4B.
Figure 4B:
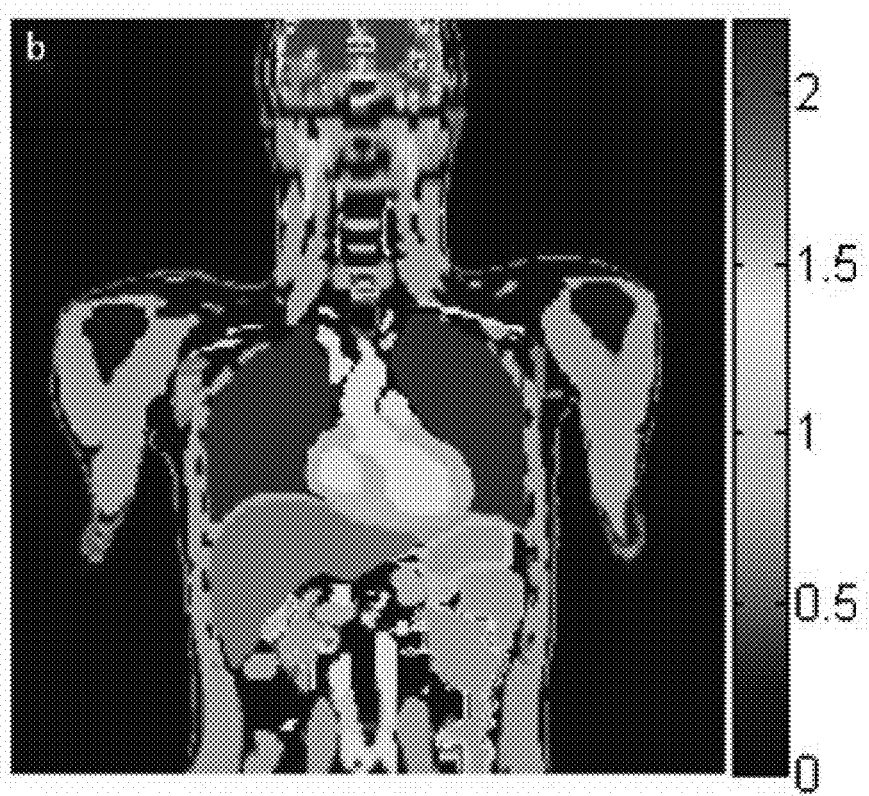

The scattering properties of the pTx coil, described by the S-matrix, depend on the load of the coil and therefore on the underlying tissue distribution and their complex conductivity (compare FIGS. 4A and 4B). In the presence of motion, the changing tissue distribution in the field of view of each coil element is characterized by a changing S-matrix. For respiratory motion, the inflow of air and the changing volume of the lungs, as well as the movement of the diaphragm and liver, changes the distribution of tissue in the upper body. Respiratory effects appear with a low rate of typically 14-18 breaths per minute (0.2 Hz-0.3 Hz) in healthy adults. Due to large tissue movements, the changes in the scattering are expected to be relatively large ($\Delta S \approx 0.1$) and prominent in all coil elements. Cardiac motion induced changes, however, are based on the volume of highly conductive blood in the heart that changes in different phases of the cardiac cycle. These changes in scattering are relatively small compared to respiratory induced effects and are most prominent in the coil elements that have a high sensitivity over the heart. The rate of cardiac-induced changes in the S-matrix are expected to be within the range of a normal heart rhythm of 60 to 100 beats per minute (1.0 Hz-1.67 Hz) for healthy adults.

Both, respiratory and cardiac motion induced changes are apparent at the same coil elements. The time dependent S-matrix can be thus modeled with three additive terms: $S_0$, which is temporally invariant and represents the coil properties and static tissue, $\Delta S_{resp}(t)$, which is the change resulting from respiratory motion, and $\Delta S_{cardiac}(t)$, which is the change resulting from cardiac motion:

$$S(t) = S_0 + \Delta S_{resp}(t) + \Delta S_{cardiac}(t) \quad [2]$$

RF-Coil Monitoring Methods (Schemes)

The S-matrix of a pTx coil can be measured with independent RF waveforms where the returned voltage $V_{i,j,ret}$ from each $V_{j,forward}$ can be identified. In this example, different RF monitoring schemes were combined with the MR-imaging RF-pulses. The imaging RF-pulse is denoted f(t) which is usually slice selective with a fixed bandwidth (e.g. Gaussian, Sinc), and g(t) as the monitoring RF-pulse function. F(f) and G(f) are denoted as their respective Fourier transforms:

$$af(t) + bg(t) = aF(w) + bG(w) \quad [3]$$

with scaling factors a and b. For MR-imaging, these waveforms should not introduce artefacts or affect the signal-to-noise ratio of the image.

Three different forms of monitoring schemes are adopted from RF-communications to MR imaging; frequency division multiplexing (FDM), time division multiplexing (TDM) and code division multiplexing (CDM). These monitoring schemes use orthogonal waveforms in frequency and time domain. For MR-imaging, two further conditions apply. Firstly, these monitoring RF waveforms should not introduce artefacts or affect the signal-to-noise ratio of the image and secondly, need to be orthogonal to the imaging RF pulse to avoid interference. For all monitoring schemes, the S-Matrix is calculated by solving the linear equation system as in Eq. 1 using MATLAB with a least-squares solution for each RF-pulse.

(Orthogonal) Frequency Division Multiplexing $$s(t) = \sum_{k=0}^{n-1} g(t) e^{-j2\pi f k \Delta f} \quad \circ\!\!-\!\!\bullet \quad S(f) = \sum_{k=0}^{n-1} G(f + k\Delta f)$$

Frequency multiplexing monitoring scheme allocates different frequency bands for each transmit channel k. Each of the channels can carry a subset of frequencies within the frequency bandwidth $BW_{channel}$. A frequency spacing $\Delta f$ separates each channel. If a small band spacing $\Delta f$ is used, the multiple of the reciprocal of the pulse length is applied to meet the orthogonality criterion (Orthogonal Frequency Division Multiplexing) and to supress RF interference between adjoin channel.

A frequency offset $f_{off}$ is applied to the centre carrier frequency $f_0$ of the imaging RF-pulse to avoid interference with the main imaging excitation RF-pulse and to avoid off-resonance excitation in the imaged object. With a given slice-select gradient, $f_{off}$ needs to large enough so that any off-resonance excitation is outside the field-of-view of the coil.

The total bandwidth B of the monitoring scheme is described by $BW_{total} \approx f_0 + T_{off} + N \cdot (\Delta f + BW_{channel})$, for N transmit channels. The total bandwidth B is limited by the bandwidth of the RF power amplifier and Analog-to-Digital converter (ADC) of the MRI system. However, the monitoring function g(t) is sensitive to motion within the resonance frequency band of the loaded coil.

Figure 5:
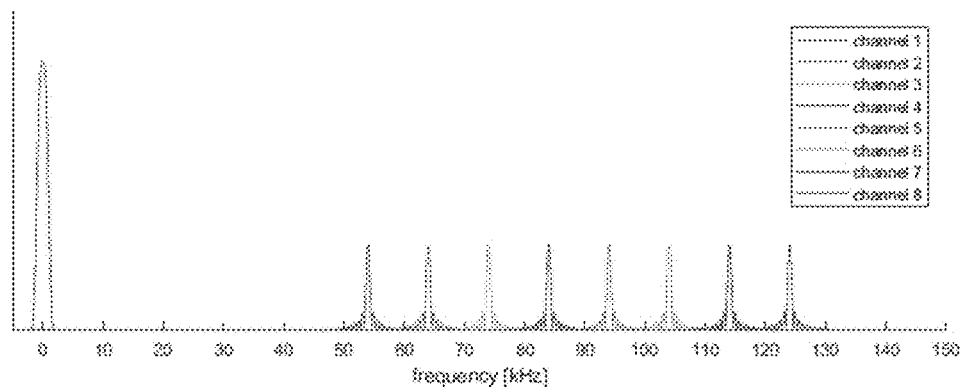
FIG. 5 shows a Fourier transform of a simulated monitoring and imaging RF-pulse. A frequency multiplexed monitoring pulse with a frequency spacing of $\Delta f=10$ kHz and frequency offset $f_{off}=54$ kHz to the imaging pulse (normalized at $f=0$ Hz with a bandwidth of 1.35 kHz) was used.

FIG. 5 shows the Fourier transform of a simulated monitoring RF-pulse function g(t) using a frequency multiplexed Fermi-Pulse with a single frequency bandwidth $B_{channel} = 1$.

Time Division Multiplexing (TDM)

$$s(t) = \sum_{k=0}^{n-1} g(t+kt_0) \circ\!\!-\!\!\bullet\; S(f) = G(f)\sum_{k=0}^{n-1} e^{j2\pi f k t_0}$$

Figure 6:
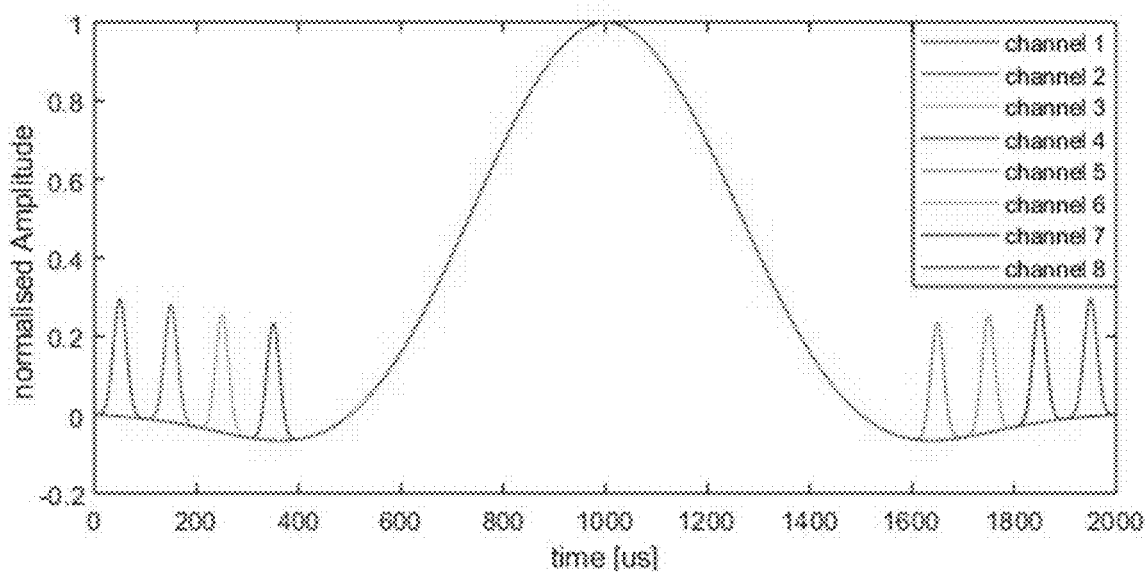
FIG. 6 shows a time-multiplexed monitoring scheme added to a Sinc-shaped RF excitation pulse in time domain.

Time division multiplexing scheme allocates different timeslots for each channel k and transmits a monitoring pulse at one channel at a time. These monitoring pulses are much shorter than the main imaging RF-pulse ($t_g \ll t_f$). Time-multiplexed monitoring pulses can have any shape (e.g. Gaussian, Fermi, Rect) and can be played out at any time during the image sequence. In this example, however, Gaussian-shaped monitoring pulses with a duration $t_g$ of 100 us were applied during the RF excitation pulse (e.g. Sinc). To avoid interference with the main pulse, the application was restricted to the low-amplitude side lobes. FIG. 6 shows time-multiplexed monitoring added to a Sinc-shaped RF excitation pulse in time domain.

Code Division Multiplexing: Random-Spike Pattern (RSP)

$$s(t) = \sum_{k=0}^{n-1} g(t)c_k(t) \circ\!\!-\!\!\bullet\; S(f) = \sum_{k=0}^{n-1} G(f)C_k(f)$$

where $c_{k_1} \perp c_{k_2}$

Code division multiplexing allows for the use of the whole bandwidth of each channel k by using an individual patter $c_{k_n}$ on each channel to encode the overlaying waveforms.

Figure 7A:
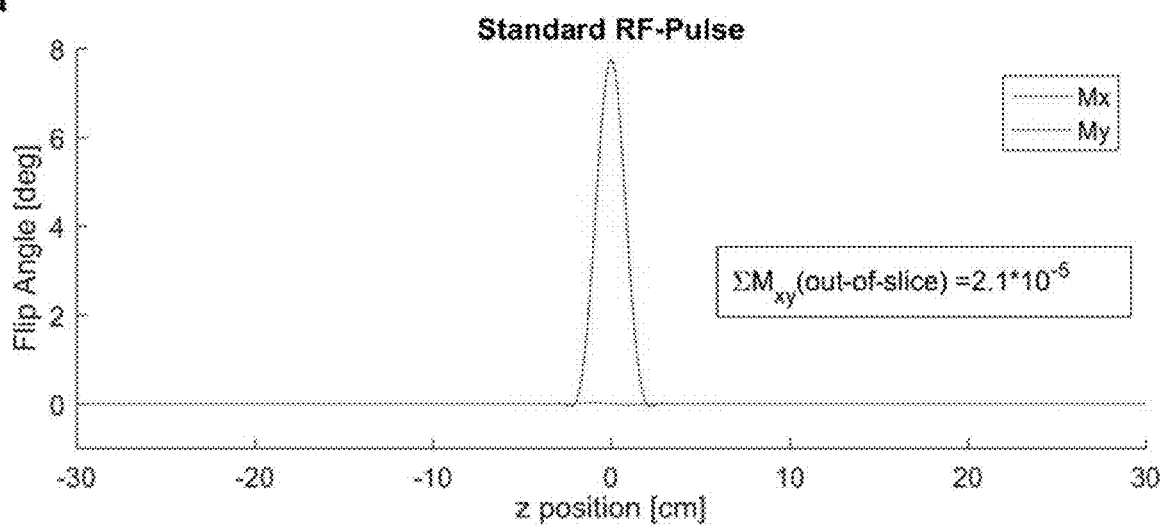
FIGS. 7A-7B are a Bloch Simulation of 7A) normal and 7B) modified RF-pulses. A white-noise like pattern can be observed in the off-resonance frequencies/non-selected slice profile, which sums up to $-2.5*10^{-4}$ and $-2.0^{\wedge}10-4$ for Mx and My, respectively.
Figure 7B:
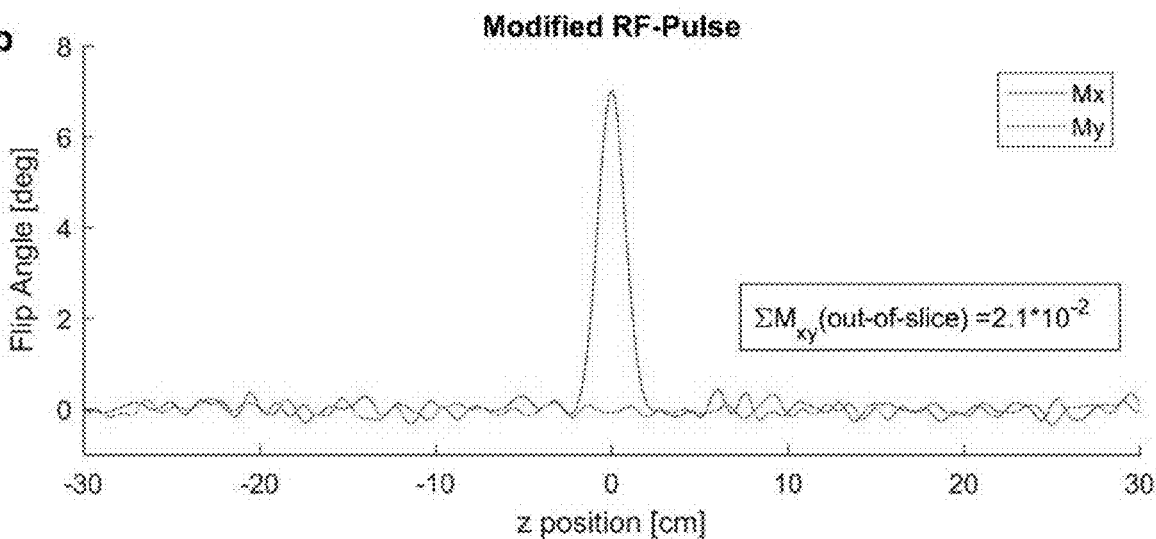

In this example, channel-independent noise patterns were used and created by ultra-short (td=3-5 us), complex rectangular RF-pulses that were alternated in four different states in the real and imaginary domain ([Real, Imaginary]=[1,0],[0,1],[0,−1],[−1,0], compare FIGS. 8A-8B) in a pseudo-random fashion to excite a broad bandwidth and to create pseudo-noise in the frequency domain. FIGS. 7A-7B are a Bloch Simulation of FIG. 7A normal and FIG. 7B modified RF-pulses. A white-noise like pattern can be observed in the off-resonance frequencies/non-selected slice profile, which sums up to −2.5*10^−4 and −2.0^10−4 for Mx and My respectively. Each transmit channel was given a different pseudo-random and channel-independent pattern. Therefore, each channel differs in time and frequency domain and the orthogonality criterion is met.

Restricting the randomness of the pattern so that all four different states occur within a small number of consecutive monitoring pulses, results in a suppression of lower frequencies. This helps to minimize noise and artefact appearance close to the imaging center frequency, i.e. selected slice profile. All different monitoring pulse states occur with an equal number during the imaging pulse to keep the net magnetization close to zero.

Methods

Measurements were made on a 7T MRI Scanner (VB17, Step 2.3, Siemens, Erlangen, Germany) with an 8-channel, dipole cardiac transmit/receive array on a cylindric water phantom and one subject. Directional couplers (DICOs) are built into each of the RF-transmission lines, as part of the pTx safety system, to measure the forwarded and reflected RF-waveforms. The OFM and RSP schemes were used to acquire the S-Matrix during image acquisition. Different amplitudes of the monitoring RF-waveform were used to investigate SNR of the motion signal and image noise. For OFM, different frequency offsets were used to quantify image artefacts.

The cardiac signal was identified using an independent component analysis as in reference (2). Respiratory motion was identified using a principal component analysis on the S-Matrix data, where the largest component was identified as breathing.

The noise was calculated by subtracting the filtered (Savitzky-Golay filter(6)) from the unfiltered cardiac signal and taking this standard deviation as the magnitude of noise. The mean peak amplitude of the cardiac signal, divided by this noise, is the SNR of the cardiac signal.

Retrospective Gating

Imaging was performed using a 2D GRE cine sequence where the RF-pulses were modified, as described above, to enable simultaneous S-matrix measurements. Either the extracted cardiac signal or ECG was utilized for cardiac gating and the k-space data was re-binned accordingly. The PULSAR MATLAB toolbox (7) was used for image reconstruction.

Results

An example of the S-matrix, calculated using the modified RF-pulses, is shown in FIGS. 9A-9D. The extracted cardiac signal had a SNR of 4.4, 7.5, 10.4 and 13.7 for a spike amplitude of 5%, 10%, 15% and 20% of that of the imaging RF-pulse, respectively. Using only the reflection of the normal imaging RF-pulse, a SNR of 7.9 can be achieved (as in ref. (4)).

Figure 8A:
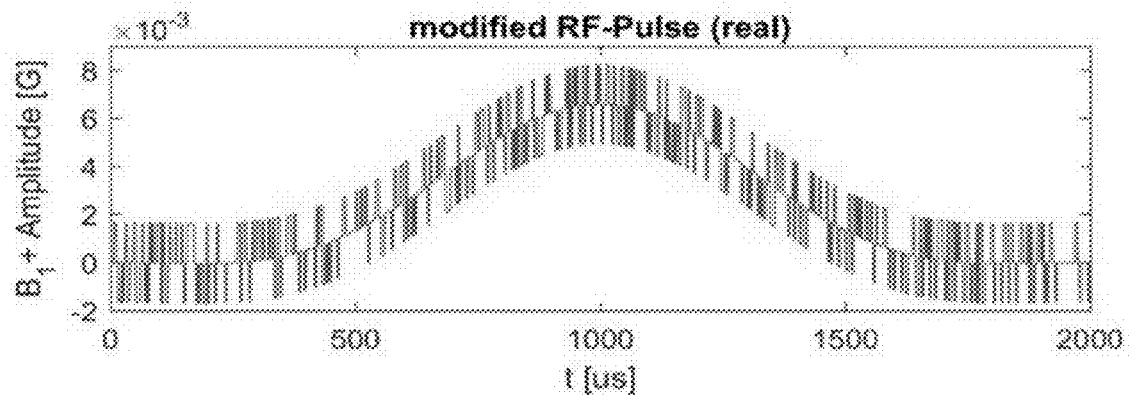
FIGS. 8A-8B show a modified RF-pulse with a Random Spike Pattern (RSP) monitoring scheme.
Figure 8B:
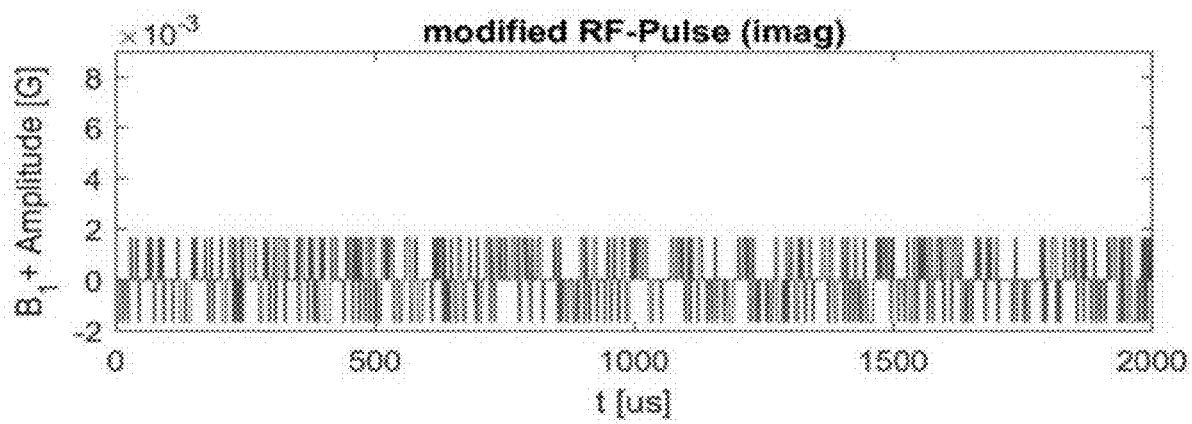
Figures 10A, 10B, 10C, 10D, 10E:
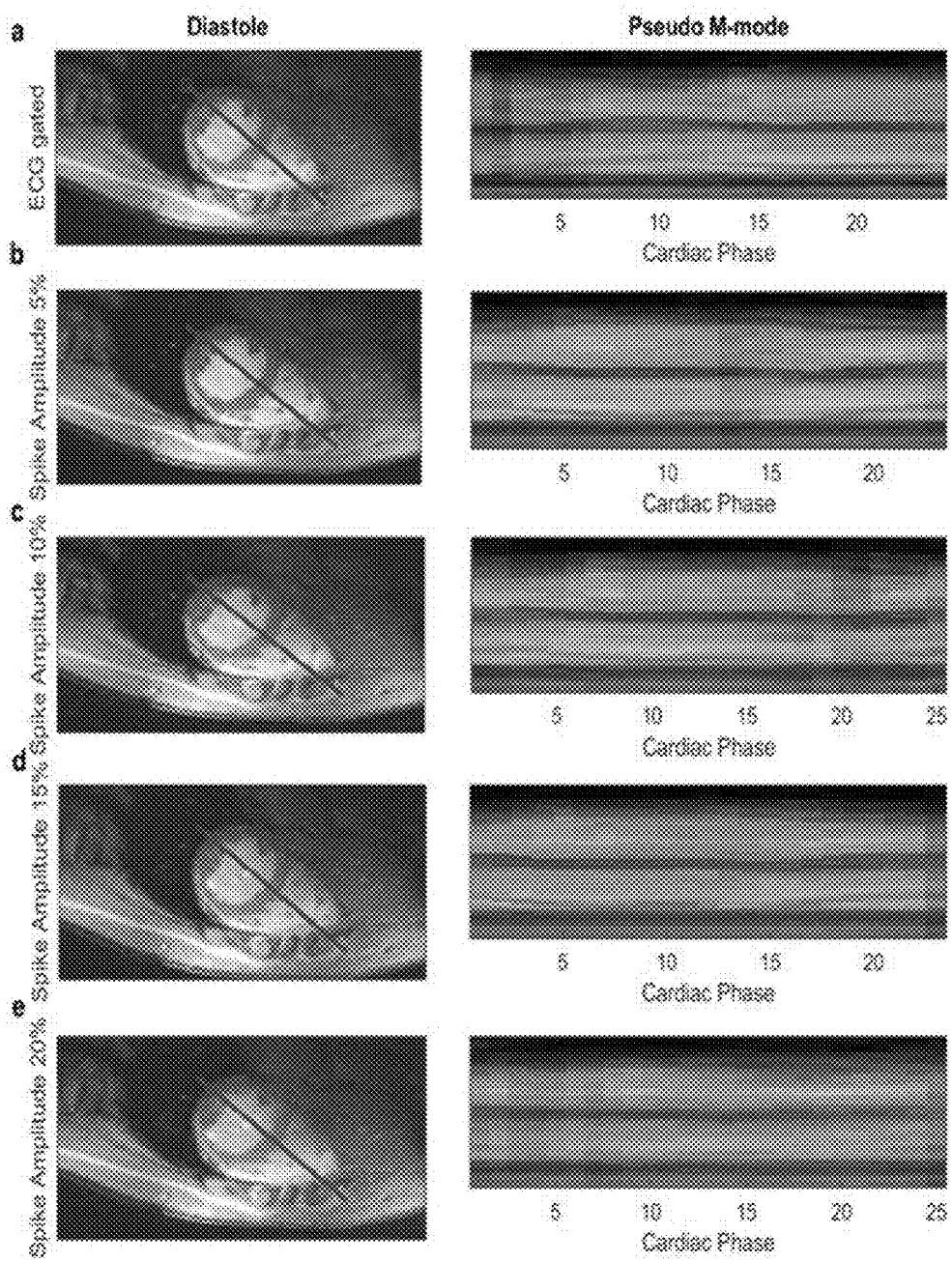
FIGS. 10A-10E: 2D GRE CINE images are shown (GRAPPA factor=2; 35 reference lines; TR=34 ms, flip angle=8°). Images were reconstructed using an ECG (FIG. 10A) and the cardiac signal extracted from the scattering matrix.

Bloch simulations of the modified RF-pulses revealed a broad bandwidth excitation with white noise like excitation (compare FIGS. 8A-8B). The induced net magnetization out-of-slice remained close to zero with the sum of Mxy of 0.018°. The added energy per pulse ranged from 0.5% to 14% for an overlaid monitoring amplitude of 5% to 20%.

All images were successfully reconstructed with minimal artefacts or blurring (compare FIGS. 10A-10E).

Discussion

This example demonstrated the measurement of the S-matrix of a pTx coil during image acquisition can be obtained and the cardiac signal can be estimated for all tested monitoring amplitudes. The SNR of the cardiac signal may be dependent on the magnitude of the monitoring amplitudes and higher for amplitudes of 15% and 20% than that using only the reflection of the standard imaging RF-pulse. The present monitoring scheme adds up to 14% to the energy of the pulse and adds noise in off-frequencies with a low amplitude (compare FIGS. 4A-4B).

Retrospectively cardiac gated 2D-CINE images show the suitability of this monitoring scheme at 7T with minimal artefacts or blurring.

Conclusion

Small, random and ultra-short RF-pulses can be used to monitor the scattering matrix of a pTx coil and to estimate a cardiac signal with high SNR during normal image acquisition at 7T MRI, which enables retrospective cardiac gating of image acquisition without prolonging the sequence and with only minimal effects on SAR and image quality.

REFERENCES—EXAMPLE 2

1. Suttie J J, Delabarre L, Pitcher A, et al. 7 Tesla (T) human cardiovascular magnetic resonance imaging using FLASH and SSFP to assess cardiac function: Validation against 1.5T and 3T. NMR Biomed. 2012; 25:27-34. doi: 10.1002/nbm.1708.

2. Jaeschke S H F, Hess A T, Robson M D. Contact-free Cardiac Motion Estimation using the Scatter of a Parallel Transmit Coil at 7T MRI. In: Proc. Intl. Soc. Mag. Reson. Med. Honolulu; 2017. p. 3262.
3. Hess A T, Tunnicliffe E M, Rodgers C T, Robson M D. Diaphragm position can be accurately estimated from the scattering of a parallel transmit RF coil at 7 T. Magn. Reson. Med. 2017; 0. doi: 10.1002/mrm.26866.
4. Jaeschke S H F, Robson M D, Hess A T. Evaluating the Influence of B1-Shimming on Contact-free Cardiac Gating using Scatter of a Parallel Transmit Coil at 7T MRI. In: Proc. Intl. Soc. Mag. Reson. Med. 25; 2017. p. 1131.
5. Jaeschke S H F, Robson M D, Hess A T. Cardiac gating using scattering of an 8-channel parallel transmit coil at 7T. Magn. Reson. Med. [Internet] 2017; 0. doi: 10.1002/mrm.27038.
6. Savitzky A, Golay M J E. Smoothing and Differentiation of Data by Simplified Least Squares Procedures. Anal. Chem. 1964; 36:1627-1639. doi: 10.1021/ac60214a047.
7. Ji JIMX, Son JBUM, Rane S D. PULSAR: A MATLAB Toolbox for Parallel Magnetic Resonance Imaging Using Array Coils and Multiple Channel Receivers. 1:24-36. doi: 10.1002/cmr.b.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about y".

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Therefore, at least the following is claimed:

1. A method for extraction of subject motion from multi-transmit electrical coupling in magnetic resonance imaging of the subject, comprising:
positioning a subject in association with a magnetic resonance scanner, wherein the magnetic resonance scanner has a plurality of transmit coils;
starting one or more MR imaging pulse sequences with the scanner, wherein the one or more MR imaging pulse sequences each comprise a plurality of imaging RF pulses;
starting one or more monitoring schemes with the scanner, wherein the one or more monitoring schemes comprise a plurality of monitoring RF pulses overlaid on the one or more MR imaging pulse sequences;
collecting one or more scattering matrix (S-matrix) measurements over a period of time using the scanner, wherein the one or more S-matrix measurements include measured information from the one or more imaging RF pulses overlaid with the plurality of monitoring RF pulses;
extracting one or more subject motion signals from the one or more S-matrix measurements;
reconstructing one or more images of a region of interest of the subject gated to the one or more subject motion signals; and
outputting the reconstructed images.

2. The method of claim 1, wherein the overlaid monitoring RF pulses include a frequency offset in relation to the centering frequency of the MR imaging pulse sequences selected to avoid interference with an imaging slice of the MR imaging pulse sequences to avoid off-resonance excitation in the imaged object, and wherein the monitoring RF pulses include a sufficient frequency spacing to cope with potential side-lobes.

3. The method of claim 1, wherein the overlaid monitoring RF pulses include an Orthogonal Frequency Multiplexing (ORM) monitoring scheme using frequency modulation RF-pulses for each transmit channel for each of the transmit coils.

4. The method of claim 1, wherein the overlaid monitoring RF pulses include ultra-short RF pulses, alternated in a pseudo-random fashion in the real and imaginary domain to create pseudo-noise in the frequency domain of the monitoring RF pulses.

5. The method of claim 1, wherein the overlaid monitoring RF pulses include a random spike pattern (RSP) scheme based on channel-independent noise patterns.

6. The method of claim 1, wherein the overlaid monitoring RF pulses include a time-division multiplex (TDM) scheme that allocates different timeslots for each transmit channel for each of the transmit coils and transmits a monitoring pulse at one channel at a time.

7. The method of claim 1, wherein the plurality of imaging RF pulses are part of a gradient echo (GRE) sequence, an inversion recovery sequence, or a balanced steady state free precession sequence, individually or in combination.

8. The method of claim 1, wherein the plurality of imaging RF pulses are frequency multiplexed pulses, parallel transmit spokes, or parallel transmit spirals, individually or in combination.

9. The method of claim 1, wherein the each of the plurality of imaging RF pulses are the same on each individual transmit coil of the plurality of transmit coils of the scanner.

10. The method of claim 1, wherein an imaging RF pulse on at least one individual transmit coil of the plurality of transmit coils is different than the pulses on the other transmit coils of the plurality of transmit coils.

11. The method of claim 2, wherein the plurality of monitoring RF pulses comprise random and/or pseudo-random spike pattern RF pulses at an offset frequency from the center frequency of one or more MR imaging pulses of about 0.001 hz to about 500 khz.

12. The method of claim 4, wherein the plurality of monitoring RF pulses have an ultra-short duration of less than about 10 µs.

13. The method of claim 1, wherein the sum of the amplitudes of the monitoring RF pulses is zero, or the induced net magnetization from the monitoring RF pulses is zero or both.

14. The method of claim 1, wherein the one or more monitoring schemes are configured to avoid inducing interference with the image excitation by the monitoring RF pulses keeping interference, if present, below a noise floor of the image excitation.

15. The method of claim 1, wherein each of the plurality of monitoring RF pulses are different on each individual channel of each transmit coil of the plurality of transmit coils of the scanner and differ by a channel offset.

16. The method of claim 15, wherein the channel offset is a time offset, a frequency offset, or both, or wherein the channel offset is a natural-number multiple of the reciprocal of the monitoring pulse length.

17. The method of claim 1, wherein the monitoring RF pulse signals on each channel are configured to not interfere with each other and the sum of dot products of each channel is zero.

18. The method of claim 1, wherein the one or more subject motion signals are a cardiac signal, a respiratory signal, or both.

19. The method of claim 1, wherein one of the one or more subject motion signals is a cardiac signal identified with an independent component analysis.

20. The method of claim 1, wherein one of the of the one or more subject motion signals is a respiratory signal identified with a principal component analysis.

* * * * *